United States Patent
Nagai et al.

(10) Patent No.: US 11,690,989 B2
(45) Date of Patent: Jul. 4, 2023

(54) MICRONEEDLE ARRAY AND METHOD FOR PRODUCING THE SAME

(71) Applicant: Nissha Co., Ltd., Kyoto (JP)

(72) Inventors: Hiroyuki Nagai, Kyoto (JP); Kensaku Akita, Kyoto (JP); Masateru Chiyama, Kyoto (JP)

(73) Assignee: Nissha Co., Ltd., Kyoto (JP)

( * ) Notice: Subject to any disclaimer, the term of this patent is extended or adjusted under 35 U.S.C. 154(b) by 831 days.

(21) Appl. No.: 16/201,300

(22) Filed: Nov. 27, 2018

(65) Prior Publication Data

US 2019/0134368 A1    May 9, 2019

Related U.S. Application Data

(63) Continuation of application No. PCT/JP2017/019528, filed on May 25, 2017.

(30) Foreign Application Priority Data

May 31, 2016    (JP) ................................. 2016-108263

(51) Int. Cl.
*B29C 45/14*    (2006.01)
*A61M 37/00*    (2006.01)
(Continued)

(52) U.S. Cl.
CPC ........ *A61M 37/0015* (2013.01); *A61M 37/00* (2013.01); *B29C 39/10* (2013.01);
(Continued)

(58) Field of Classification Search
CPC ................ B29C 45/14; B81C 1/00111; A61M 2037/0053
See application file for complete search history.

(56) References Cited

U.S. PATENT DOCUMENTS

2011/0028905 A1    2/2011 Takada
2012/0041412 A1    2/2012 Roth et al.
(Continued)

FOREIGN PATENT DOCUMENTS

JP    2008-029710 A    2/2008
JP    2008-228959 A    10/2008
(Continued)

OTHER PUBLICATIONS

Extended European Search Report dated Jun. 4, 2019 for corresponding European Application No. 17806519.9, 6 pp.
(Continued)

*Primary Examiner* — Timothy Kennedy
*Assistant Examiner* — Farah Taufiq
(74) *Attorney, Agent, or Firm* — United IP Counselors, LLC

(57) ABSTRACT

Provided is an inexpensive microneedle array with little dimensional error that can control, with high precision, the amount of a predetermined component to be introduced to the inner part of the skin, and a production method for this microneedle array. A foundation that is insoluble or sparingly soluble in inner part of the skin is overlaid on a mold. A plurality of frustum-shaped protrusions, which are insoluble or sparingly soluble in the raw material liquid, provided on a first main surface of the foundation are fit into a plurality of cone-shaped recesses. The raw material liquid in the plurality of cone-shaped recesses dries and, as a result, a plurality of microneedles, which are dissolvable in the inner part of the skin, are fixed to tip surfaces of the plurality of frustum-shaped protrusions.

16 Claims, 13 Drawing Sheets

(51) Int. Cl.
   *B81B 1/00* (2006.01)
   *B29C 39/10* (2006.01)
   *B81C 1/00* (2006.01)
   *B29K 101/12* (2006.01)
   *B29L 31/00* (2006.01)

(52) U.S. Cl.
   CPC ............... *B29C 45/14* (2013.01); *B81B 1/00* (2013.01); *B81B 1/008* (2013.01); *B81C 1/00* (2013.01); *B81C 1/00111* (2013.01); *A61M 2037/0023* (2013.01); *A61M 2037/0046* (2013.01); *A61M 2037/0053* (2013.01); *B29K 2101/12* (2013.01); *B29L 2031/756* (2013.01); *B29L 2031/7544* (2013.01); *B81B 2203/0361* (2013.01); *B81C 2201/034* (2013.01)

(56) References Cited

U.S. PATENT DOCUMENTS

| | | | | |
|---|---|---|---|---|
| 2013/0296790 A1* | 11/2013 | Masaoka | ........... | A61M 37/0015 604/173 |
| 2016/0001053 A1* | 1/2016 | Quan | ................ | A61M 37/0015 604/46 |
| 2017/0057124 A1* | 3/2017 | Wakamatsu | ........... | A61K 47/36 |
| 2017/0266427 A1* | 9/2017 | Nishimura | ........... | A61K 9/0021 |
| 2018/0066938 A1* | 3/2018 | Hu | ........................ | G01F 22/00 |

FOREIGN PATENT DOCUMENTS

| | | | | | |
|---|---|---|---|---|---|
| JP | 2009201956 A | * | 9/2009 | ........ | A61M 37/0015 |
| JP | 2013-517907 A | | 5/2013 | | |
| JP | 2013-153866 A | | 8/2013 | | |
| JP | 2013-158601 A | | 8/2013 | | |
| JP | 5538897 B2 | | 7/2014 | | |
| JP | 2015-136422 A | | 7/2015 | | |
| JP | 2015136422 A | * | 7/2015 | ........ | A61M 37/0015 |
| JP | 2015-217042 A | | 12/2015 | | |
| WO | 2012/057345 A1 | | 5/2012 | | |
| WO | 2015/122838 A1 | | 8/2015 | | |
| WO | WO-2015122838 A1 | * | 8/2015 | ........... | A61K 9/0021 |
| WO | 2016/039418 A1 | | 3/2016 | | |

OTHER PUBLICATIONS

International Search Report dated Aug. 29, 2017 for corresponding foreign Application No. PCT/JP2017/019528, 2 pp.

\* cited by examiner

MICRONEEDLE ARRAY AND METHOD FOR PRODUCING THE SAME

CROSS-REFERENCE TO RELATED APPLICATIONS

This application is a continuation application of International Application No. PCT/JP2017/019528, filed on May 25, 2017, which claims priority under 35 U.S.C. § 119 to Japanese Patent Application No. 2016-108263, filed on May 31, 2016. The entire disclosures of both applications are hereby incorporated herein by reference in their entities.

BACKGROUND

Technical Field

The present disclosure generally relates to a microneedle array and a production method for the same.

Background Information

Conventionally, one means of noninvasively administering a drug or the like via the body surface of an organism, such as the skin or a mucous membrane, is to perform transdermal administration via a transdermal patch. Furthermore, to efficiently absorb a drug or the like from a transdermal patch into the body, a preparation called a microneedle sheet or a microneedle patch has been developed whereon the drug is adhered to, is coated with or is adsorbed by minute needles. The minute needles have a high aspect ratio, which are referred to as so-called microneedles, and those minute needles are disposed in an array on a sheet. For example, Patent Citation 1 (Japanese Patent No. 5538897) discloses a technique in which a drug is provided on microneedles, which perforate the stratum corneum, thereby introducing the medicine as far as an inner part of the skin at a part that is deeper than the stratum corneum.

When, for example, delivering a drug using microneedles, it is preferable that the amount of the drug introduced to the inner part of the skin be as accurate as possible. To introduce an accurate amount of a drug, it is important to adjust, with high precision, the amount of the drug contained on the microneedle array and also suppress variations in the amount of the drug that the microneedles deliver to the inner part of the skin. However, in the production method of the microneedle array described in Patent Citation 1, it is difficult to manage the amount of the drug contained in one microneedle and, as a result, it is difficult to provide a uniform amount of the drug throughout the microneedle array. Additionally, careful work is needed to remove only the portion containing the drug and, as such, it is difficult to inspect and quantify the amount of the drug at the time of production, and it is difficult to guarantee the amount of the drug when made into a pharmaceutical product. Moreover, the resulting increase in inspection labor leads to the microneedle array becoming more expensive. Furthermore, when delivering a drug using a microneedle array, cases are likely to occur in which not all of the portion of the microneedle array that contains the drug is introduced to the inner part of the skin.

However, with microneedle arrays, it is not enough simply to control the amount of the drug with high precision. For the microneedles to effectively perforate the stratum corneum, it is also important to reduce the dimensional error of the shape of the microneedles.

BRIEF SUMMARY

It is an object of the present disclosure to provide an inexpensive microneedle array that has little dimensional error and that can control, with high precision, the amount of a predetermined component to be administered to the inner part of the skin, and a production method for this microneedle array.

A plurality of aspects are described below as the technical solution. These aspects can be arbitrarily combined as needed.

A method of producing a microneedle array according to one aspect of the present invention includes an injection step of injecting a predetermined amount of a raw material liquid into each cone-shaped recess of a mold having a plurality of cone-shaped recesses, the predetermined amount being less than a volume of the cone-shaped recess; a tip forming step of overlaying a foundation that is insoluble or sparingly soluble in the raw material liquid on the mold, mating a plurality of frustum-shaped protrusions or columnar protrusions, provided on a first main surface of the foundation, with the plurality of cone-shaped recesses, drying the raw material liquid in the plurality of cone-shaped recesses thereby fixing a plurality of cone-shaped tips that are dissolvable in an inner part of skin to a tip surface of each of the plurality of frustum-shaped protrusions or columnar protrusions; and a mold release step of removing the foundation from the mold, and pulling out a microneedle array in which the cone-shaped tips are fixed to each of the frustum-shaped protrusions or the columnar protrusions of the foundation and the cone-shaped tips are formed at a position a predetermined height away from the first main surface of the foundation.

According to the method of producing the microneedle array having the configuration described above, a predetermined amount of the raw material liquid can be injected into the cone-shaped recesses with high precision. As a result, the amount of the component in the cone-shaped tips that is carried into the inner part of the skin by the frustum-shaped protrusions or the columnar protrusions of the foundation can be adjusted with high precision. Moreover, in the tip forming step, the cone-shaped tips are fixed to the tip surfaces of the frustum-shaped protrusions or the columnar protrusions. As such, the cone-shaped tips are not likely to separate when being introduced into the inner part of the skin, but also will easily release after penetrating. Therefore, a microneedle array can be formed whereby it is easier to administer the entire microneedle array into the inner part of the skin. Furthermore, a push-in margin, equivalent to the predetermined height, for pushing the cone-shaped tips into the inner part of the skin can be ensured by the frustum-shaped protrusions or the columnar protrusions. As such, the reliability of the cone-shaped tips reaching the predetermined depth in the inner part of the skin is improved and, as a result, it is easier to improve the control precision of the amount of component to be administered.

It is acceptable that the method of producing a microneedle array further includes an inspection step of immersing the microneedle array in a solvent capable of dissolving the cone-shaped tips to dissolve the plurality of cone-shaped tips and make a solution, and analyzing a component contained in each of the microneedle array based on the solution. In this case, for example, it is possible to conduct a sampling inspection in a short period of time in which the entire microneedle array is immersed in a solvent capable of dissolving the cone-shaped tips, and the cone-shaped tips are separated from the foundation and the plurality of frustum-shaped protrusions or the columnar protrusions and dissolved, and the component contained in one microneedle array is analyzed. As such, the component contained in the cone-shaped tips can be frequently inspected and easily inspected and analyzed and, as such, the component contained in the microneedle array can be controlled with high precision in the production process of the microneedle array.

It is acceptable that the method of producing a microneedle array further includes a preparation step of preparing the foundation including the plurality of frustum-shaped protrusions or the plurality of columnar protrusions by injection molding. As a result of this configuration, the foundation is formed by injection molding and, as such, the foundation including the plurality of frustum-shaped protrusions or columnar protrusions can easily be mass produced, which facilitates the suppression of the price of the microneedle array.

It is acceptable that, in the production method for the microneedle array, in the preparation step, a roughening treatment is performed or a dimple is formed at a contacting portion of the plurality of frustum-shaped protrusions or the plurality of columnar protrusions, the contacting portion being where the cone-shaped tips are to be fixed. As a result of this configuration, the cone-shaped tip enters the roughened portion or the dimple provided at the contacting portion and, as such, the fixing force fixing the cone-shaped tip to the tip surface and/or the periphery of the frustum-shaped protrusion or the columnar protrusion can be improved. As a result, the cone-shaped tip is less likely to separate prior to being introduced into the inner part of the skin, and high-precision control of the amount of the component can be stably realized when administering the predetermined component to the inner part of the skin.

It is acceptable that, in the production method for the microneedle array, in the preparation step, a hydrophilic treatment is performed on the contacting portion of the plurality of frustum-shaped protrusions or the plurality of columnar protrusions, the contacting portion being where the cone-shaped tips are to be fixed, such that a hydrophilicity of the contacting portion is made greater than a hydrophilicity of a material of the foundation. As a result of this configuration, the raw material liquid adheres to the contacting portions of the frustum-shaped protrusions or the columnar protrusions due to the hydrophilic treatment, and this leads to an improvement in the fixing force. As a result, high-precision control of the amount of the component can be stably realized when administering the predetermined component to the inner part of the skin.

It is acceptable that, in the method of producing the microneedle array, in the tip forming step, while the foundation is overlaid on the mold, a gap is formed between a side wall of each of the cone-shaped recesses and a side surface of each of the frustum-shaped protrusions or the columnar protrusions and the raw material liquid is fed into the gap, thereby forming the cone-shaped tip up to the side surface of each of the frustum-shaped protrusions or the columnar protrusions above a position that is a predetermined height away from the first main surface. As a result of this configuration, the cone-shaped tips are fixed to the frustum-shaped protrusions or the columnar protrusions at the side surfaces of the frustum-shaped protrusions or the columnar protrusions, and this leads to an improvement in the fixing force. As a result, high-precision control of the amount of the component can be stably realized when administering the predetermined component to the inner part of the skin.

It is acceptable that, in the method of producing the microneedle array, in the tip forming step, the foundation and the mold are arranged such that the side surface of each of the frustum-shaped protrusions or columnar protrusions abuts against the side wall of each of the cone-shaped recesses due to the foundation being overlaid on the mold. As a result of this configuration, foundations including frustum-shaped protrusions or columnar protrusions of varying heights can be formed using the same mold and, as such, the number of molds kept in stock, for example, can be reduced. Thus, production cost can be reduced and an inexpensive microneedle array can be provided.

A microneedle array according to another aspect of the present invention includes a resin foundation including, on a first main surface, a plurality of frustum-shaped protrusions or columnar protrusions that are insoluble or sparingly soluble in a raw material liquid, the resin foundation being formed from a thermoplastic resin that is insoluble or sparingly soluble in the inner part of the skin; and a plurality of cone-shaped tips a predetermined height away from the first main surface of the resin foundation and fixed to the plurality of frustum-shaped protrusions or columnar protrusions, the plurality of cone-shaped tips being dissolvable in the inner part of the skin. The resin foundation includes a dimple formed in a region where each of the plurality of frustum-shaped protrusions or columnar protrusions is covered by one of the cone-shaped tips.

With the microneedle array configured in this manner, the fixing force fixing the cone-shaped tip to the frustum-shaped protrusion or columnar protrusion can be improved as a result of the cone-shaped tip entering the dimple provided at the contacting portion of the frustum-shaped protrusion or the columnar protrusion. As a result, the cone-shaped tip is less likely to separate prior to being introduced into the inner part of the skin, and high-precision control of the amount of the component can be stably obtained when administering the predetermined component to the inner part of the skin.

A microneedle array according to another aspect of the present invention includes a resin foundation including, on a first main surface, a plurality of frustum-shaped protrusions or columnar protrusions that are insoluble or sparingly soluble in a raw material liquid, the resin foundation being formed from a thermoplastic resin that is insoluble or sparingly soluble in the inner part of the skin; and a plurality of cone-shaped tips a predetermined height away from the first main surface of the resin foundation and fixed to the plurality of frustum-shaped protrusions or columnar protrusions, the plurality of cone-shaped tips being dissolvable in the inner part of the skin. In the plurality of frustum-shaped protrusions or the columnar protrusions of the resin foundation, a hydrophilicity of a contacting portion that contacts the cone-shaped tips is higher than a hydrophilicity of a material of the resin foundation.

With the microneedle array configured in this manner, the raw material liquid adheres to the frustum-shaped protrusions or the columnar protrusions due to the hydrophilicity of the contacting portions being high, and this leads to an improvement in the fixing force. As a result, high-precision control of the amount of the component can be stably realized when administering the predetermined component to the inner part of the skin. Additionally, the raw material liquid is less likely to adhere to the portions where the hydrophilicity is low. As such, reducing the hydrophilicity of the portions where the raw material liquid is not intended to adhere enables the amount of the cone-shaped tip to be more easily controlled and facilitates the enhancements of the control precision of the amount of the component to be administered.

A microneedle array according to one aspect of the present invention includes a resin foundation including, on a first main surface, a plurality of frustum-shaped protrusions or columnar protrusions that are insoluble or sparingly soluble in a raw material liquid, the resin foundation being formed from a thermoplastic resin that is insoluble or sparingly soluble in the inner part of the skin; and a plurality of cone-shaped tips a predetermined height away from the first main surface of the resin foundation and fixed to the plurality of frustum-shaped protrusions or columnar protrusions, the plurality of cone-shaped tips being dissolvable in the inner part of the skin. In the plurality of frustum-shaped protrusions or columnar protrusions of the resin foundation, a roughness of a contacting portion that contacts the cone-shaped tips is higher than a roughness of portions other than the contacting portion.

With the microneedle array configured in this manner, the fixing force fixing the cone-shaped tip to the frustum-shaped protrusion or columnar protrusion can be improved as a result of the cone-shaped tip entering the irregular unevenness of the rough portion provided at the contacting portion of the frustum-shaped protrusion or the columnar protrusion. As a result, the cone-shaped tip is less likely to separate prior to being introduced into the inner part of the skin, and high-precision control of the amount of the component can be stably obtained when administering the predetermined component to the inner part of the skin. Additionally, the roughness of the portion of the frustum-shaped protrusions or the columnar protrusions that contact the skin when penetrating the skin can be made not to increase. As such, the friction resistance when penetrating the skin can be reduced and the introduction of the portions of the frustum-shaped protrusions or the columnar protrusions up to the predetermined position in the inner part of the skin can be facilitated.

The microneedle array according to the present disclosure is inexpensive and has little dimensional error. Additionally, using this microneedle array enables the amount of a predetermined component, to be administered to the inner part of the skin, to be controlled with high precision. Moreover, the production method of the microneedle array according to the present disclosure is suitable for the production of the microneedle array according to the present disclosure.

BRIEF DESCRIPTION OF THE DRAWINGS

Referring now to the attached drawings which form a part of this original disclosure.

DETAILED DESCRIPTION OF THE EMBODIMENTS (1) Appearance of Microneedle Array

Figure 1:
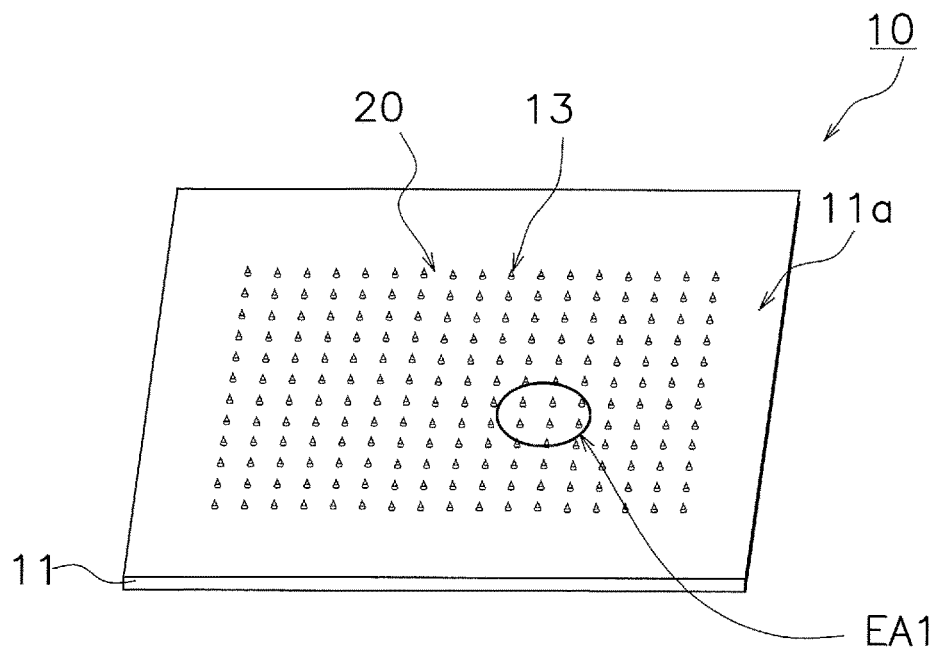
FIG. 1 is a perspective view illustrating an example of a microneedle array according to an embodiment of the present invention.
Figure 2:
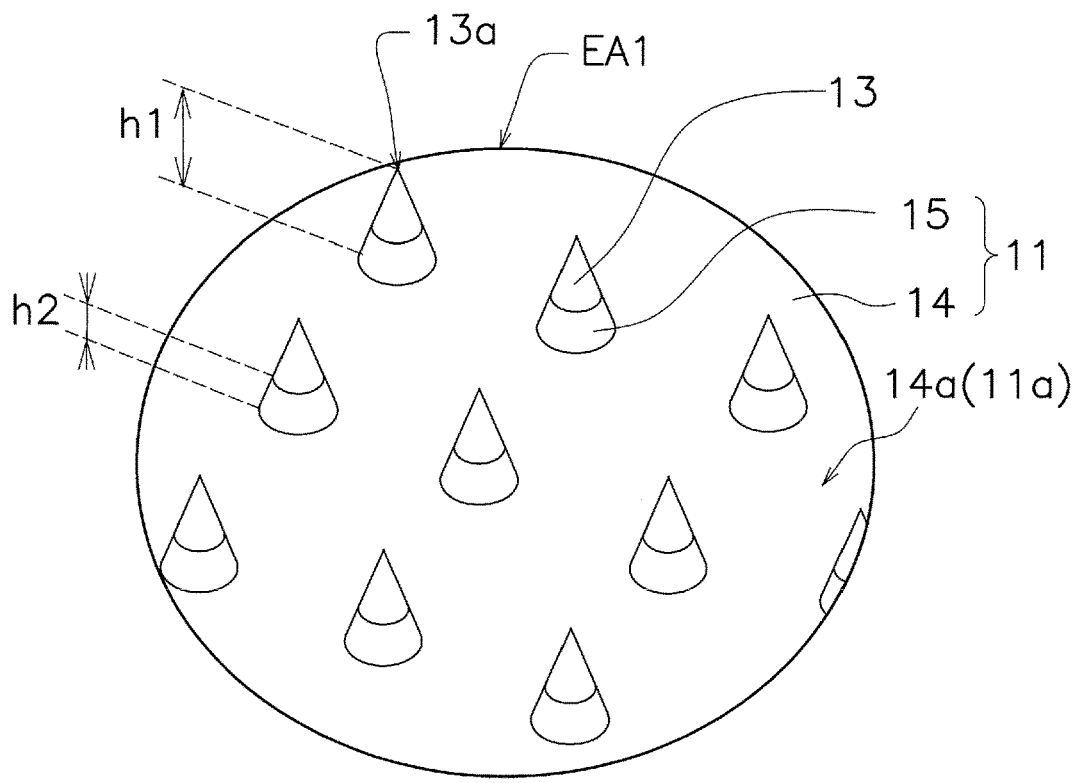
FIG. 2 is a partially enlarged perspective view of a portion of the microneedle array illustrated in FIG. 1.

FIG. 1 illustrates the microneedle array according to an embodiment of the present invention, and FIG. 2 is a partially enlarged view of the microneedle array illustrated in FIG. 1. The microneedle array 10 includes a base material 11, and a plurality of microneedles 13 formed on a first main surface 11a of the base material 11. In one example, the microneedles 13 are arranged in a matrix of m rows×n columns. In this case, m and n are nonnegative numbers greater than or equal to 2.

(1-1) Base Material 11

The base material 11 includes a single layer foundation 14 and a plurality of frustum-shaped protrusions 15 on a first main surface 14a of the foundation 14. In this case, the first main surface 14a of the foundation 14 is the first main surface 11a of the base material 11. The plurality of frustum-shaped protrusions 15 is formed from a thermoplastic resin and is integrated with the foundation 14. Examples of thermoplastic resins that can be used to form the base material 11 include polylactic acid, polycarbonate, polysulfone, polyetheretherketone, poly(lactic-co-glycolic acid) (PLGA), and polyglycolic acid.

Figure 3:
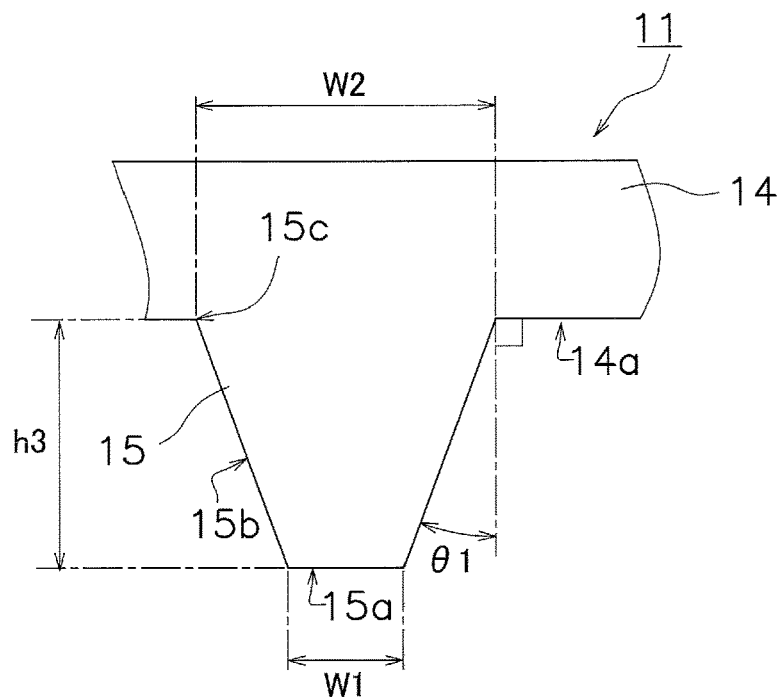
FIG. 3 is a partially enlarged cross-sectional view of a portion of a base material of the microneedle array illustrated in FIG. 1.

FIG. 3 is an enlarged drawing of one of the frustum-shaped protrusions 15 and, from the perspective of FIG. 3, depicts a tip surface 15a of the frustum-shaped protrusion in a downward facing state. The reason the tip surface 15a is facing downward in FIG. 3 is because, in the production method of the microneedle array 10 (described later), the tip surface 15a is faced downward in order to be dipped in a raw material liquid 200 accumulated in a mold 50 (see FIG. 5).

The frustum-shaped protrusions 15 according to the present embodiment are truncated circular cones. The frustum-shaped protrusions that can be used in the present invention have a shape obtained by cutting off the tip of the cone to form a tip surface. Accordingly, the cross-sectional shape of the frustum-shaped protrusions may be a shape other than round, and the protrusions may for example, be truncated pyramids instead of truncated circular cones. In the example described in the present embodiment, the base material 11 includes a plurality of the frustum-shaped protrusions 15. However, a configuration is possible in which the base material 11 includes a plurality of columnar protrusions instead of the plurality of frustum-shaped protrusions 15. Alternatively, the base material 11 may include a combination of frustum-shaped protrusions and columnar protrusions.

Each of the frustum-shaped protrusions 15 has a tip surface 15a and a side surface 15b. An angle θ1 of a generating line of the side surface 15b of the frustum-shaped protrusion 15 (see FIG. 3) is an angle formed between the generating line of the side surface 15b and an imaginary line that is perpendicular to the plane of the foundation 14 and is tangent to the side surface 15b. In FIG. 3, the first main surface 14a of the foundation 14 is flat, and the plane of the foundation 14 tangent to the side surface 15b of the frustum-shaped protrusion 15 matches the first main surface 14a. The angle θ1 of the side surface 15b of the frustum-shaped protrusion 15 is obtained by adding 5° to 15° to an angle θ2 (see FIG. 4) of a generating line of a side wall 51b of a cone-shaped recess 51 (described later).

In one example, a width W1 of the tip surface 15a of the frustum-shaped protrusion 15 is set between 100 μm and 500 μm. Since the frustum-shaped protrusion 15 is a truncated circular cone, the width W1 is equivalent to the diameter of the tip surface 15a. A bottom 15c of the frustum-shaped protrusion 15 is a boundary between the frustum-shaped protrusion 15 and the first main surface 14a of the foundation 14. In one example, a width W2 of the bottom 15c is set between 150 μm and 2500 μm. Since the frustum-shaped protrusion 15 is a truncated circular cone, the width W2 is equivalent to the diameter of the bottom 15c.

In one example, a height h3 of the frustum-shaped protrusion 15 is set between 100 μm and 600 μm. It is possible to adjust the depth the microneedles 13 reach when the microneedles 13 are pressed into the inner part of the skin by adjusting the height h3 of the frustum-shaped protrusions 15.

(1-2) Microneedles 13

Each of the microneedles 13 is a cone-shaped tip formed on the tip surface 15a of each of the frustum-shaped protrusions 15. As described previously, the frustum-shaped protrusions 15 are a part of the base material 11 and are not the microneedles 13 themselves. The microneedles 13 are parts that enter into and can dissolve in the inner part of the skin of a human. The function of the microneedles 13 is to deliver a predetermined component contained therein to the inner part of the skin. A height h1 of a tip position of each of the microneedles 13 is defined as the height from the first main surface 14a of the foundation 14 to the tip 13a of the microneedle 13 and, in one example, is from 200 μm to 1000 μm. The height h1 of microneedles 13 to be used on human skin is preferably from 500 μm to 600 μm. In one example, when the height h1 of the tip position of the microneedle 13 is set between 200 μm and 1000 μm, a length h2 from the lower portion of the microneedle 13 to the foundation 14 (lower portion height) is from 100 μm to 500 μm. For example, when the height h1 of the tip position of the microneedle 13 is set between 500 μm and 600 μm, the lower portion height h2 is set between 200 μm and 300 μm. From the perspective of ensuring administration depth, the lower portion height is preferably 100 μm or greater. Additionally, from the perspective of ensuring the dose of the medicine, the lower portion height h2 is preferably no greater than ⅔ the height h1 of the tip position of the microneedle 13. That is, the lower portion height h2 is preferably set in the range of 100 μm≤h2≤⅔×h1.

Figure 14:
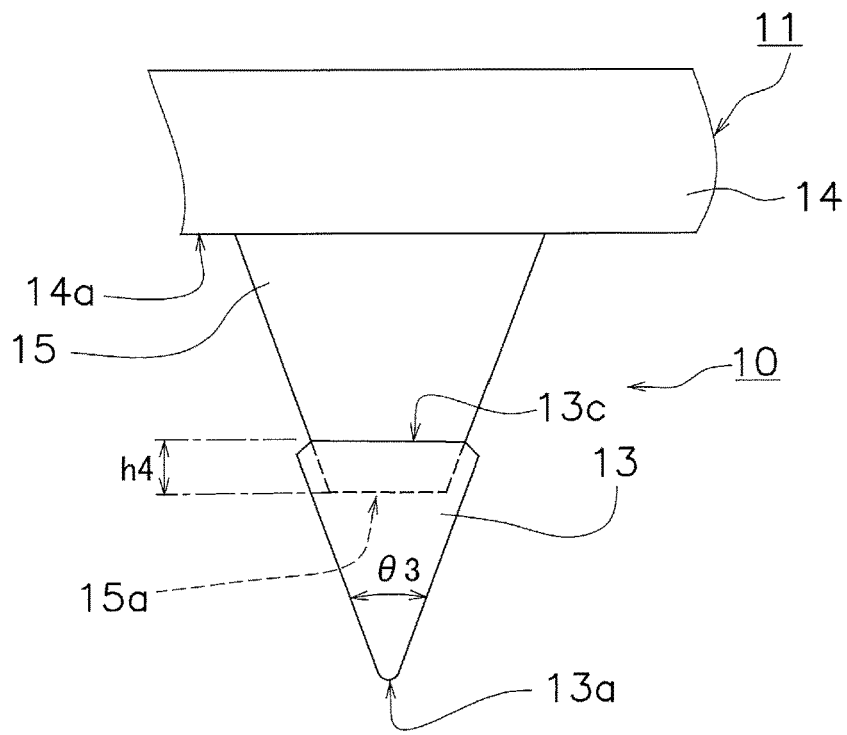
FIG. 14 is a partially enlarged side view schematically illustrating one of the microneedles formed by the mold and the base material illustrated in FIG. 13.

Moreover, in order to facilitate the microneedles 13 penetrating the skin, an angle θ3 of the microneedle 13 is preferably no greater than 40° (see FIG. 14). The angle θ3 is the maximum angle formed by the two sides that appear when cutting through the tip 13a on a plane perpendicular to the first main surface 14a of the foundation 14. The radius of the rounding on the tip 13a of the microneedle 13 is preferably not greater than 15 μm. However, in order to provide the microneedles 13 with sufficient strength, the angle θ3 of the microneedle 13 is preferably no less than 20°. Additionally, the radius of the rounding on the tip 13a is preferably not less than 1 μm.

(2) Production of Microneedle Array

The microneedle array 10 is produced using the base material 11 described above and a mold 50 illustrated in FIG. 4. It is required that the mold 50 has a shape that corresponds to the shape of the base material 11 and, as such, is prepared together with the base material 11. FIGS. 5 to 8 illustrate an overview of the production process of the microneedle array 10 in which the base material 11 and the mold 50 are used.

(2-1) Mold 50

The mold 50 has a flat plate-like shape. A plurality of cone-shaped recesses 51 is formed in a surface 50a of the mold 50. In one example, the cone-shaped recesses 51 are arranged in a matrix of m rows×n columns, corresponding to the microneedles 13 described above.

It is sufficient that the mold 50 be formed from a hygienic material that is not affected by the raw material liquid of the microneedles 13, and this hygienic material preferably has high gas permeability. For example, the mold 50 may be formed from a plastic, an elastomer, or a ceramic. It is preferable that the material of the mold 50 be sterilized using an autoclave or radiation prior to use. The material forming the mold 50 is preferably silicone rubber. Preferable examples of the plastic forming the mold 50 include polytetrafluoroethylene, polycarbonate, polysulfone, and polyetheretherketone.

An alignment mark (not illustrated in the drawings) is formed on the surface 50a of the mold 50. This alignment mark is read by a CCD camera (not illustrated in the drawings) of a microneedle array production apparatus 100, and is used to relatively align the microneedle array production apparatus 100 with the mold 50.

The cone-shaped recesses 51 illustrated here are circular cones. Accordingly, the cone-shaped recesses 51 may have a shape other than round. For example, the cone-shaped recesses 51 may have a pyramid shape. In the example described in the present embodiment, the mold 50 includes a plurality of the cone-shaped recesses 51. However, a configuration is possible in which, instead of the cone-shaped recesses, the mold 50 includes recesses in which the tip is cone shaped and the portion continuing from the tip has another shape. Examples of the other shape include a columnar shape.

Figure 4:
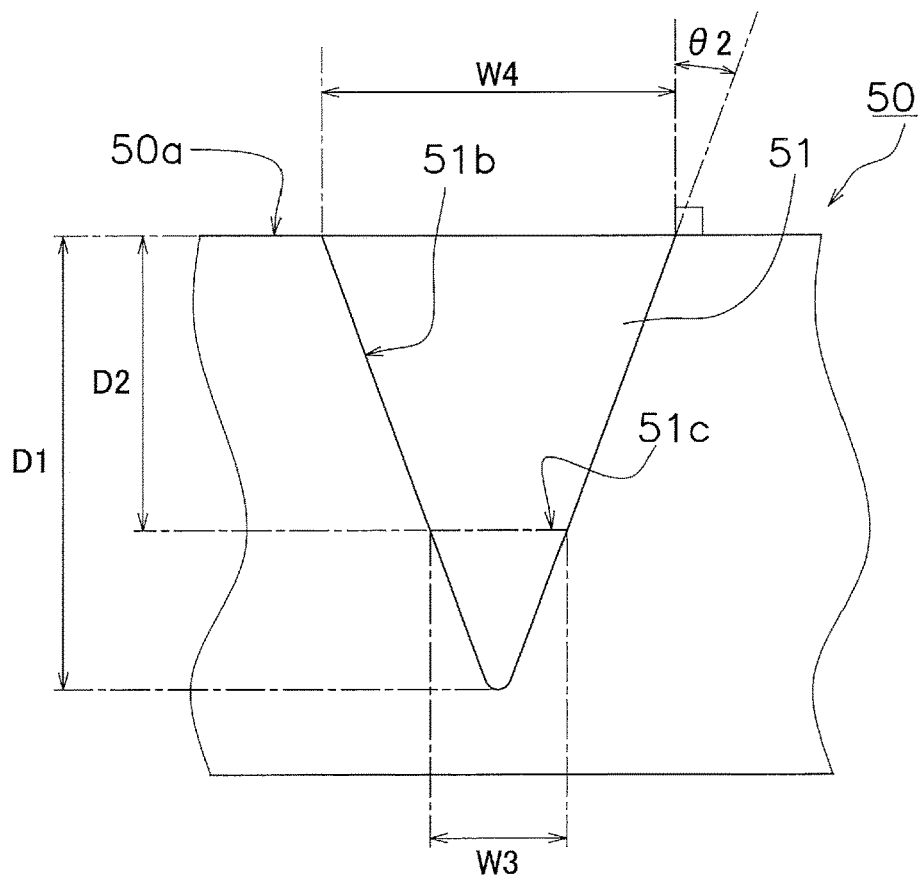
FIG. 4 is a partially enlarged cross-sectional view of a portion of a mold of the microneedle array.

As illustrated in FIG. 4, the angle θ2 between the generating line of the side wall 51b of each cone-shaped recess 51 in the mold 50 and the direction perpendicular to the surface 50a of the mold 50 is set in a range of 10° to 50°, for example. From the perspectives of ease of production and facilitating penetration into the skin, the value of the angle θ2 is preferably from 20° to 40°. The frustum-shaped protrusion 15 illustrated in FIG. 3 is formed so as to fit, without gaps, into the cone-shaped recess 51 illustrated in FIG. 4. The location 51c depicted by the dot-dash line in FIG. 4 substantially matches the tip surface 15a of the frustum-shaped protrusion 15. Accordingly, a depth D2 from the surface 50a of the mold 50 to the dot-dash line location 51c is set the same as the height h3 of the frustum-shaped protrusion 15.

A depth D1 of the cone-shaped recess 51 is set on the basis of the height h1 of the tip position of the microneedle 13. Space from the depth D1 up to the depth D2 of the cone-shaped recess 51 is filled with the raw material liquid 200. Since the microneedles 13 are formed as a result of the raw material liquid 200 drying, when determining the depth D1 the shrinkage rate due to the drying is taken into consideration.

In order for the frustum-shaped protrusion 15 to fit, without gaps, into the cone-shaped recess 51, a width W4 of an opening in the surface 50a of the cone-shaped recess 51 is set to be equivalent to or smaller than the width W2 of the bottom 15c of the frustum-shaped protrusion 15. Specifically, it is preferable that these widths are set such that width W4<width W2 so that the frustum-shaped protrusion 15 reliably contacts the cone-shaped recess 51 when the base material 11 is overlaid on the mold 50. Likewise, in order for the frustum-shaped protrusion 15 to mate, without gaps, with the cone-shaped recess 51, the width W3 of the dot-dash line location 51c of the cone-shaped recess 51 is set to be equivalent to or smaller than the width W1 of the tip surface 15a of the frustum-shaped protrusion 15.

(2-2) Microneedle Array Production Apparatus 100

Figure 5:
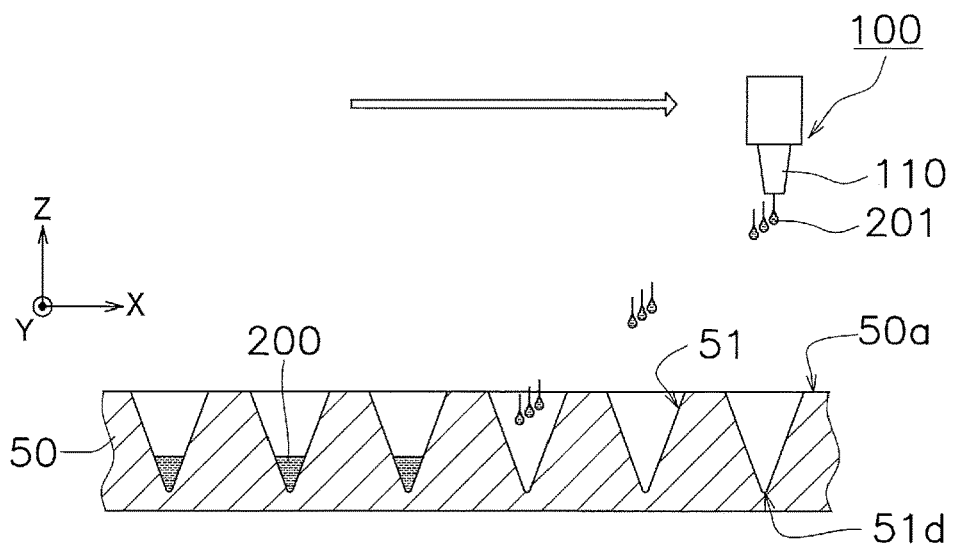
FIG. 5 is a schematic cross-sectional view illustrating an example of an injection step of the microneedle array.

The microneedle array production apparatus 100 illustrated in FIG. 5 includes a droplet discharge device 110 that discharges the raw material liquid 200 of the microneedles 13, and an XYZ stage (not illustrated in the drawings). The mold 50 is placed on the XYZ stage of the microneedle array production apparatus 100. The mold 50 has a flat plate-like shape and, as such, the microneedle array production apparatus 100 is configured to automatically relatively align the droplet discharge device 110 with the cone-shaped recesses 51 by moving the XYZ stage parallel to the XY plane. The droplet discharge device 110 discharges a plurality of droplets 201 of the raw material liquid 200 into each cone-shaped recess 51, thereby injecting a predetermined amount of the raw material liquid 200 into each cone-shaped recess 51. In one example, the raw material liquid 200 is discharged from the droplet discharge device 110 as the droplets 201, and the amount of each of the droplets 201 is set in a range of 0.01 nanoliters/droplet to 10 nanoliters/droplet.

In a preferable configuration, the raw material liquid 200 is injected such that the droplets 201 land on a portion of the cone-shaped recess 51 that is closer to the bottom 51d than to the dot-dash line location 51c. If the droplets 201 land higher than the dot-dash line location 51c, the raw material liquid 200 may become trapped between the side wall 51b of the cone-shaped recess 51 and the side surface 15b of the frustum-shaped protrusion 15. If the raw material liquid 200 becomes trapped between the side wall 51b and the side surface 15b, problems will occur such as the amount of the component changing, the raw material liquid 200 leaking from between the side wall 51b and the side surface 15b, and the error of the height h1 of the tip position of the microneedle 13 increasing.

From the perspective of sharpening the tips of the microneedles 13 to facilitate penetration into the skin, the tip of the cone-shaped recess 51, that is, the curvature radius of the bottom 15d is preferably set in a range of 1 μm to 20 μm.

(2-3) Raw Material Liquid 200

The raw material liquid 200 of the microneedles 13 is, for example, a solution obtained by dissolving a solid raw material in water, a mixed solvent of water and alcohol, or another solvent, a suspension obtained by dispersing a solid raw material in water, a mixed solvent of water and alcohol, or another solvent, or a mixture thereof. The solid raw material is a polymeric substance that is harmless to the human body. Examples thereof include resins that are harmless to the human body, polysaccharides that are harmless to the human body, proteins that are harmless to the human body, and compounds derived from these that are harmless to the human body. Examples of compounds to be introduced to a human body include bioactive substances used to treat, diagnose, or prevent injury or illness.

The raw material liquid 200 is obtained by adding a bioactive substance administered to diagnose, treat, or prevent a disease to a solvent in which, for example, a water-soluble polysaccharide (including derivatives thereof and salts of the derivatives) is dissolved. The solvent of the raw material liquid 200 is evaporated off, thereby forming microneedles 13 in which the bioactive substance is contained in a polysaccharide base material. Examples of the water-soluble polysaccharide (including derivatives thereof and salts of the derivatives) include sodium chondroitin sulfate, hyaluronic acid, dextran, and carboxymethyl cellulose. Examples of the bioactive substance include insulin and growth hormone.

(2-4) Production Steps

Figure 7:
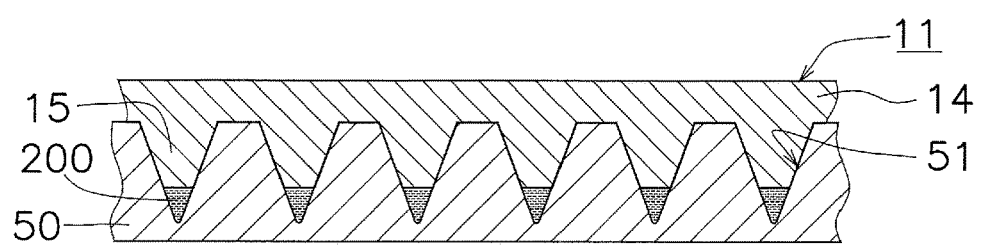
FIG. 7 is a schematic cross-sectional view for describing drying of a raw material liquid in a tip forming step.
Figure 8:
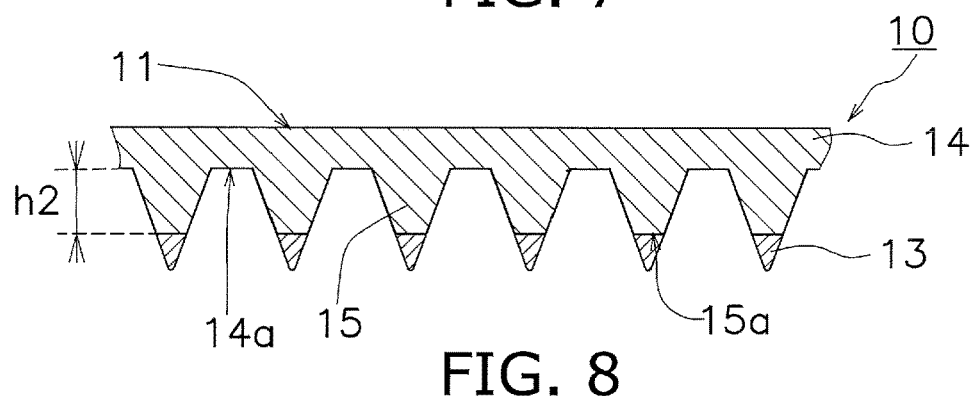
FIG. 8 is a schematic cross-sectional view illustrating the microneedle array after a mold release step.
Figure 9:
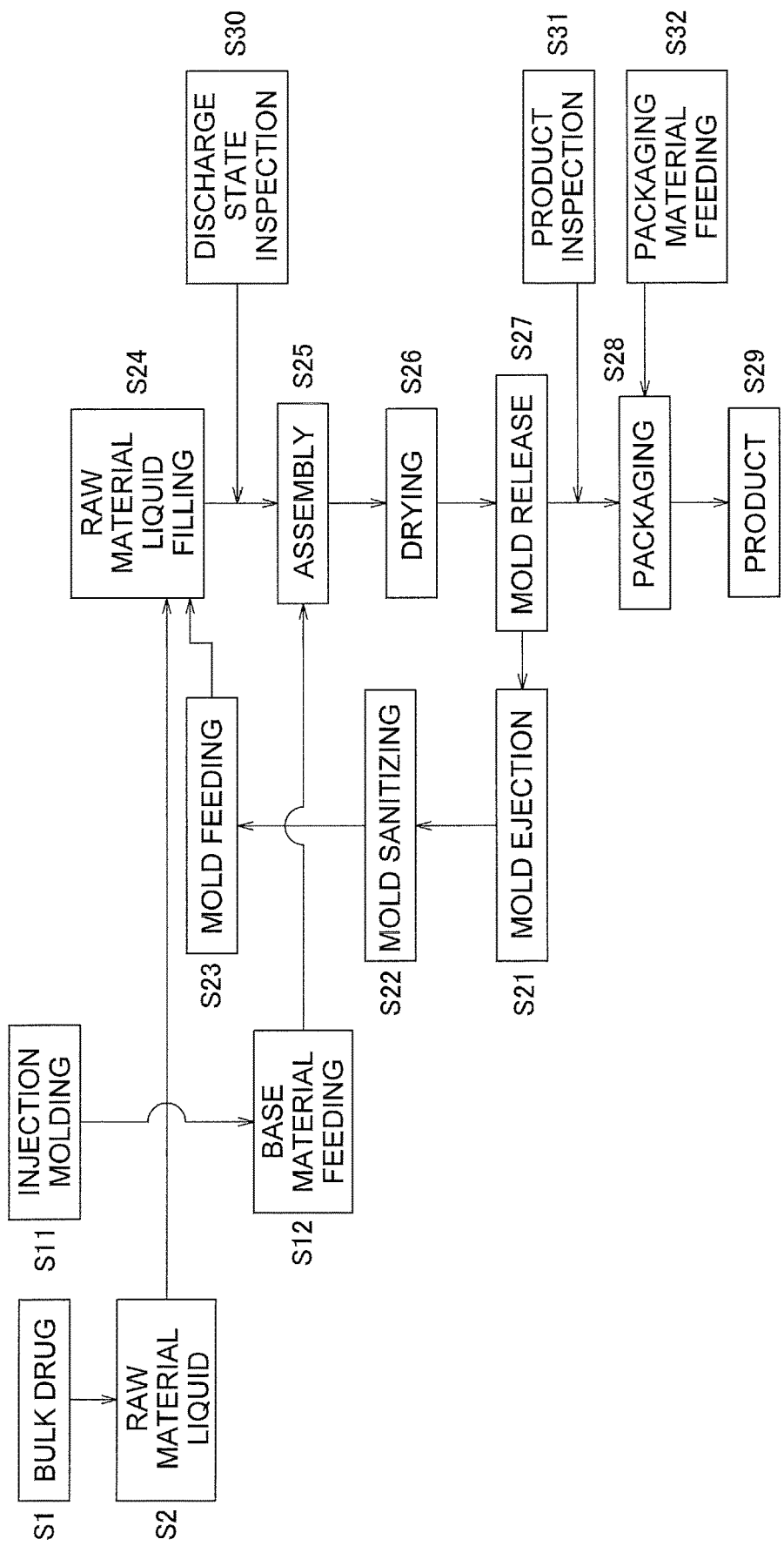
FIG. 9 is a flowchart illustrating an example of the production flow of the microneedle array.

Each step in the production is described while referencing FIGS. 5 to 9. FIG. 9 illustrates the flow of the production steps of the microneedle array 10. In the production, first, a bulk drug, for example, is prepared as the component to be administered to the inner part of the skin (step S1). A bulk drug is a chemical component of a pharmaceutical product that exhibits a desired effect. In other words, a bulk drug is the effective ingredient of a pharmaceutical product. Next, the bulk drug, the solid raw material, and the solvent are blended. As a result, the raw material liquid 200 is obtained (step S2).

In parallel with, before, or after the preparation of the raw material liquid 200, the base material 11 is prepared by injection molding (step S11). Furthermore, the mold 50 is prepared and fed (step S23). It is preferable that the prepared base material 11 and mold 50 are sanitized. The sanitizing can be carried out using, for example, an autoclave or radiation.

(2-4-1) Injection Step

In the injection step illustrated in FIG. 5, a predetermined amount, which is less than the volume of the cone-shaped recess 51, of the raw material liquid 200 is injected into each cone-shaped recess 51 in the mold 50. With the cone-shaped recesses 51 illustrated in FIG. 5, the predetermined amount is an amount equivalent to the capacity of the cone-shaped recess 51 between the depth D1 and the depth D2.

Specifically, the mold 50 fed in step S23 is placed on the XYZ stage of the microneedle array production apparatus 100. Then, the mold 50 is moved by the XYZ stage to match the coordinates on the XY plane of the cone-shaped recess 51 and the droplet discharge device 110. Is a state in which the positions of the cone-shaped recess 51 and the droplet discharge device 110 match, the droplets 201 discharged from the droplet discharge device 110 are discharged near the bottom 51d of the cone-shaped recess 51 at a location lower than the dot-dash line location 51c. This operation is repeated to inject the raw material liquid 200 in the predetermined amount into all of the cone-shaped recesses 51 (step S24).

In one example, when the raw material liquid 200 has been injected into a plurality of molds 50, a mold 50 is arbitrarily selected from the plurality of molds 50 as a sample, and a discharge state inspection on the state of the injected raw material liquid 200 is carried out (step S30). In one example, the amount and/or component of the raw material liquid 200 injected into the mold 50 is inspected in the discharge state inspection.

(2-4-2) Tip Forming Step

Figure 6:
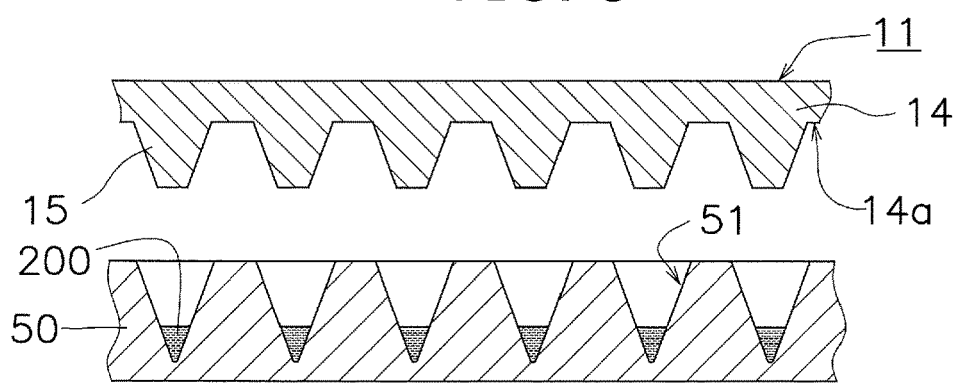
FIG. 6 is a schematic cross-sectional view for describing the overlapping of the base material on the mold in the tip forming step.

The foundation 14 of the base material 11 illustrated in FIG. 6 is overlaid on the mold 50. This step corresponds to the assembly step (step S25) depicted in FIG. 9. Since the foundation 14 is insoluble or sparingly soluble in the raw material liquid 200, the shape of the foundation 14 is maintained until the raw material liquid 200 has dried. Likewise, the plurality of frustum-shaped protrusions 15 on the first main surface 14a of the foundation 14 are insoluble or sparingly soluble in the raw material liquid 200.

As illustrated in FIG. 7, the plurality of frustum-shaped protrusions 15 are fit into the plurality of cone-shaped recesses 51. Thus, the raw material liquid 200 in the plurality of cone-shaped recesses 51 is dried while the frustum-shaped protrusions 15 are fit into the cone-shaped recesses 51 (step S26). Since the vapor of the solvent can pass through the mold 50, which is made from silicone rubber, the raw material liquid 200 can dry while the frustum-shaped protrusions 15 are fit into the cone-shaped recesses 51. The raw material liquid 200 dries in the plurality of cone-shaped recesses 51 and, as a result, the plurality of microneedles 13 are fixed to the tip surfaces 15a of the plurality of frustum-shaped protrusions 15 (see FIG. 8). The microneedles 13 dried in this manner form cone-shaped tips that are dissolvable in the inner part of the skin. Note that the drying may be performed one time or multiple times. For example, preliminary drying may be performed prior to step S26. Moreover, a configuration is possible in which additional drying is performed after the mold release step (step S27, described later).

(2-4-3) Mold Release Step

FIG. 8 illustrates a state in which the microneedle array 10 has been released from the mold 50 by the mold release step (step S27). In the mold release step, the foundation 14 is removed from the mold 50, and the microneedle array 10, in which a cone shaped tip, namely a microneedle 13, is fixed to each frustum-shaped protrusion 15 of the foundation 14, is removed. Each of the microneedles 13 is formed at a position separated the lower portion height h2, which is the height to the lower portion of the microneedles 13, from the first main surface 14a of the foundation 14 (example of position separated a predetermined height from the first main surface 14a).

From among the plurality of microneedle arrays 10 removed from molds, an arbitrary microneedle array 10 is selected and subjected to a product inspection (step S31). The product inspection step (step S31) includes an inspection step for immersing the microneedle array 10 in a solvent capable of dissolving the cone-shaped tips (i.e., the microneedles 13), dissolving the plurality of microneedles 13 in the solvent to make a solution, and analyzing the component contained in one microneedle array 10 from the solution. Since the foundation 14 and the frustum-shaped protrusions 15 are insoluble in the solution, the analysis can be conducted with high accuracy in a short amount of time.

(2-4-4) Other Steps

After the mold release step (step S31), packaging material is fed (step S32), and the completed microneedle array 10 is packaged (step S28). Then, the packaged microneedle array 10 is shipped as a product, or the like.

Additionally, the mold 50 that has been subjected to the mold release step is ejected from the production line (step S21). The ejected mold 50 is cleaned (step S22) and, thereafter, is reintroduced to the production line (step S23). It is preferable that the molds 50 that are fed to the production line have been sanitized using an autoclave or radiation. Note that when there is a concern about contamination of the mold 50, a new mold 50 may be fed without reusing the mold 50.

(3) Features

3-1

According to the production method of the microneedle array described above, a predetermined amount of the raw material liquid 200 can be injected into the cone-shaped recesses 51 with high precision. As a result, the amount of the component of the microneedles 13 (i.e., the cone-shaped tips) that is delivered to the inner part of the skin by the frustum-shaped protrusions 15 of the foundation 14 can be adjusted with high precision. In the tip forming step, the microneedles 13 are fixed to the tip surfaces 15a of the frustum-shaped protrusions 15. As such, the microneedles 13 are not likely to separate when being introduced to the inner part of the skin, and also will easily release after penetrating. Therefore, a microneedle array 10 can be formed whereby it is easier to administer the entire microneedle array 10 to the inner part of the skin. Furthermore, a push-in margin, equivalent to the lower portion height h2, for pushing the microneedles 13 to the inner part of the skin can be ensured by the frustum-shaped protrusions 15. As such, the reliability of the microneedles 13 reaching the predetermined depth in the inner part of the skin is improved and, as a result, it is easier to improve the control precision of the amount of component to be administered.

3-2

In the embodiment described above, the product inspection step is provided and, for example, it is possible to conduct a sampling inspection in a short period of time in which the microneedles 13 are quickly dissolved and separated from the foundation 14 and the plurality of frustum-shaped protrusions 15, and the component contained per one microneedle array is analyzed. Therefore, the component contained in the microneedles 13 can be frequently inspected and monitored and, as a result, the component contained in the microneedle array 10 can be controlled with high precision in the production method for the microneedle array 10.

(4) Modification Examples

While an embodiment of the present invention has been described, the present invention should not be construed as being limited thereto, and various types of modifications may be made without departing from the spirit or scope of the general inventive concept of the invention. In particular, the embodiment recited in the present specification and the plurality of modification examples described hereinafter can be combined as desired or necessary.

(4-1) Modification Example A

Figure 10:
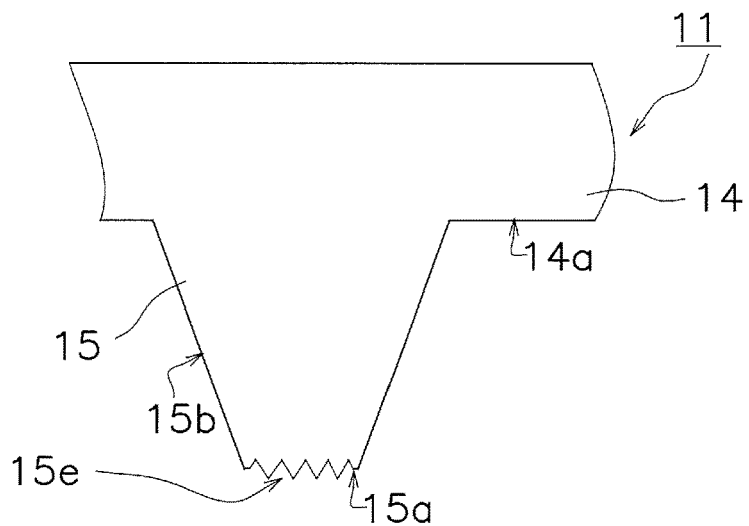
FIG. 10 is a partially enlarged cross-sectional view schematically illustrating a second example of the base material.
Figure 15:
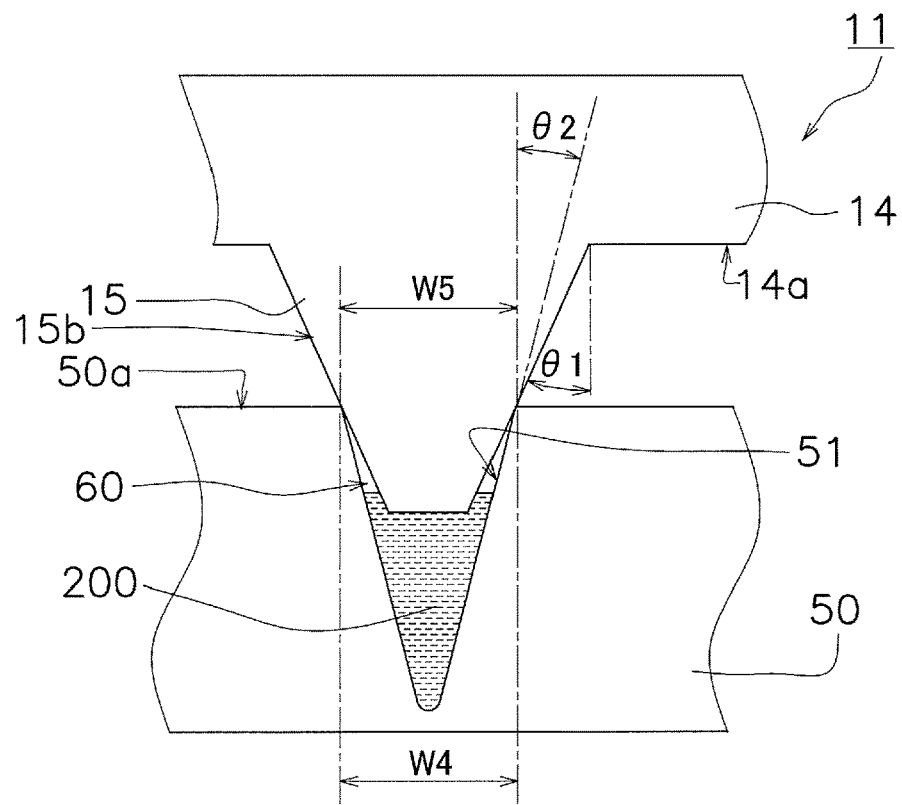
FIG. 15 is a partially enlarged cross-sectional view schematically illustrating a third example of the combination of the mold and the base material.

In the embodiment described above, the tip surface 15a of each of frustum-shaped protrusion 15 is flat. However, as illustrated in FIG. 10, a configuration is possible in which a contacting portion, which is provided on the tip surface 15a and/or the side surface 15b the microneedle 13 and which contacts the microneedle 13, is roughened. The roughened portion 15e illustrated in FIG. 15 is the tip surface 15a but, in cases in which the side surface 15b also contacts the microneedle 13, the contacting portion of the side surface 15b may also be roughened. Examples of the roughening method include a method of surfacing the bottom surface of the injection molding mold corresponding to the tip surface 15a by sandblasting or the like, and a method of setting the pitch and cusp height and cutting. Examples of a roughening treatment to be performed on the base material 11 include a chemical etching treatment with an acid or alkali, and an erosion treatment of the base material 11 using a solvent. In the erosion treatment using a solvent, the base material 11 made from injection molded thermoplastic resin is treated with a solvent that dissolves the thermoplastic resin. For example, when a thermoplastic resin that is slightly soluble in an alcohol is used for the base material 11, the base material 11 is treated with an alcohol.

(4-2) Modification Example B

In the embodiment described above, the tip surface 15a of the frustum-shaped protrusion 15 is flat. However, a configuration is possible in which the tip surface 15a is curved into a convex shape to increase contact area. In this case, the tip surface 15a of the frustum-shaped protrusion 15 is curved by subjecting the bottom surface of the injection molding mold corresponding to the tip surface 15a to rounding processing. The curvature radius of the tip surface 15a in this case is, for example, 0.05 mm or greater.

(4-3) Modification Example C

Figure 11:
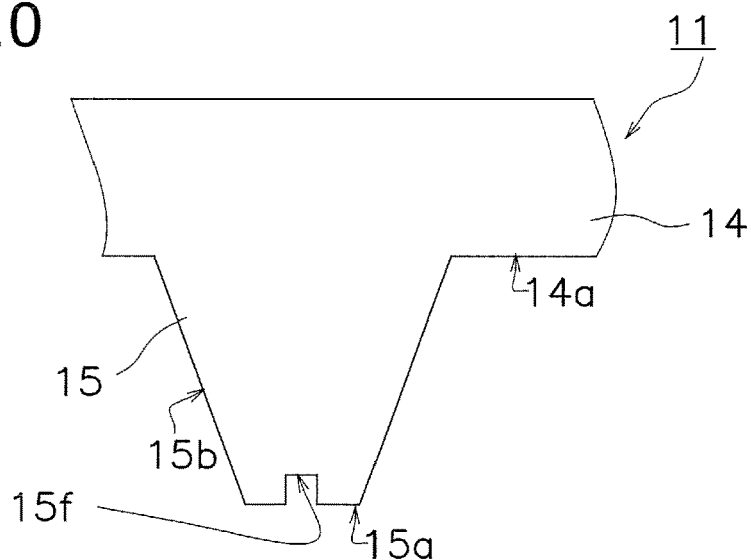
FIG. 11 is a partially enlarged cross-sectional view schematically illustrating a third example of the base material.
Figure 12:
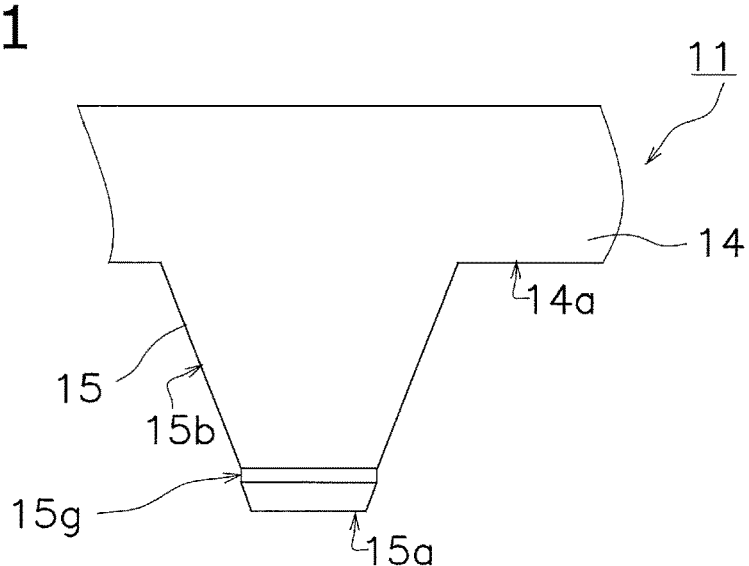
FIG. 12 is a partially enlarged cross-sectional view schematically illustrating a fourth example of the base material.

In the embodiment described above, the tip surface 15a and the side surface 15b of the frustum-shaped protrusion 15 are flat. However, a configuration is possible in which, a dimple (or step) 15f or 15g is formed as illustrated in FIGS. 11 and 12 at the contacting portion where the tip surface 15a and/or the side surface 15b contacts the microneedle 13 as illustrated in FIG. 10. That is, it is sufficient that the tip surface 15a and/or the side surface 15b have a dimple that is formed in the region where each of the plurality of frustum-shaped protrusions or columnar protrusions is covered by the cone-shaped tip (the microneedle 13). The fixing force fixing the cone-shaped tip to the frustum-shaped protrusion or columnar protrusion can be improved as a result of the cone-shaped tip (the microneedle 13) entering the dimple provided at the contacting portion of the frustum-shaped protrusion or columnar protrusion. As a result, the cone-shaped tip is less likely to separate prior to being introduced to the inner part of the skin, and high-precision control of the amount of the component can be stably realized when administering the predetermined component to the inner part of the skin.

(4-4) Modification Example D

When the raw material liquid 200 is an aqueous solution, a hydrophilic treatment may be performed in a preparation step. In the preparation step, it is preferable that hydrophilic treatment be performed such that the hydrophilicity of the contacting portion of each frustum-shaped protrusion 15 where the cone-shaped tip (i.e., the microneedle 13) is fixed is made greater than the hydrophilicity of the portions other than the contacting portion. Examples of the hydrophilic treatment include plasma discharge treatment in which the base material 11 is subjected to plasma discharge, and ultraviolet irradiation treatment in which the base material 11 is irradiated with ultraviolet rays. The hydrophilic treatment can be performed on the first main surface 11a of the base material 11 but, for example, can also be performed on the tip surface 15a by exposing only the tip surface 15a. Performing the hydrophilic treatment on only the portion intended as the contacting portion will make it less likely for the raw material liquid 200 to adhere to locations that are not intended as the contacting portion.

(4-5) Modification Example E

Figure 13:
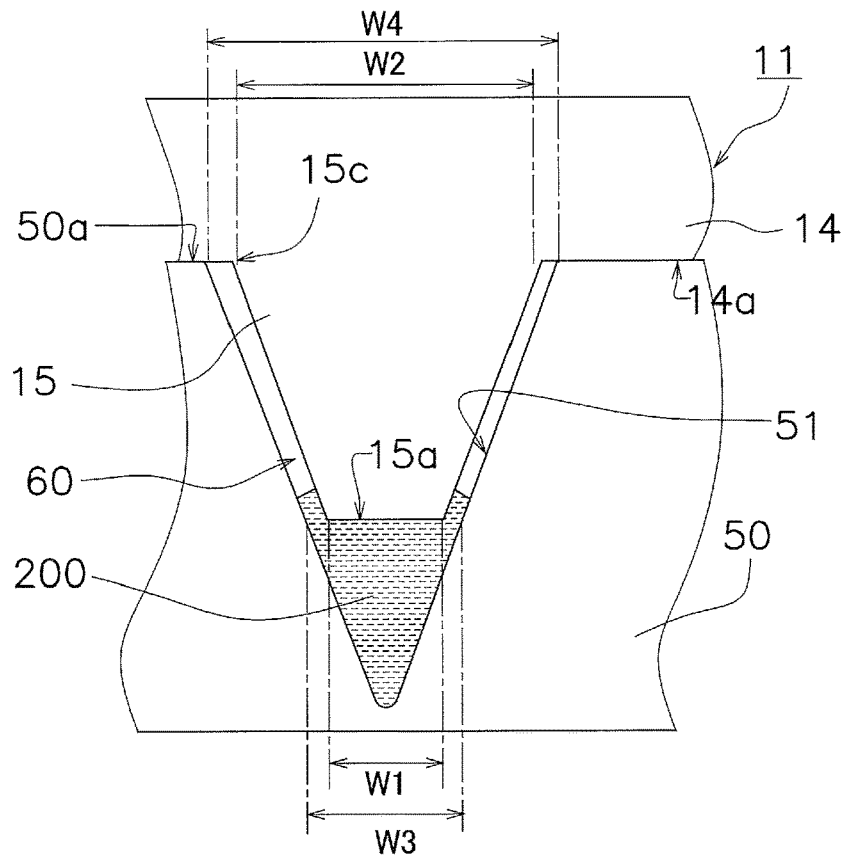
FIG. 13 is a partially enlarged cross-sectional view schematically illustrating a second example of a combination of the mold and the base material.

In the embodiment described above, a case is described in which the frustum-shaped protrusions 15 fit into the cone-shaped recesses 51 without any gaps. However, as illustrated in FIG. 13, a configuration is possible in which a gap 60 is formed between the frustum-shaped protrusion 15 and the cone-shaped recess 51. To realize this configuration, the width of the frustum-shaped protrusion 15 illustrated in FIG. 13 is formed so as to become narrower than the width of the cone-shaped recess 51. For example, in a state in which the first main surface 14a of the foundation 14 is abutted against the surface 50a of the mold 50, the width W1 of the tip surface 15a of the frustum-shaped protrusion 15 is set to be smaller than the width W3 at the same position of the cone-shaped recess 51, and the width W2 of the bottom 15c of the frustum-shaped protrusion 15 is set to be smaller than the width W4 of the opening in the surface 50a of the cone-shaped recess 51 (W1<W3 and W2<W4). In this case, the angle θ1 of generating line of the side surface 15b of the frustum-shaped protrusion 15 (see FIG. 3) is preferably set to an angle obtained by adding an angle selected from a range of, for example, −15° to 15° to the angle θ2 of generating line of the side wall 51b of the cone-shaped recess 51 (see FIG. 4). From the perspectives of ease of production and facilitating penetration into the skin, the angle θ2 is set in a range of 10° to 50°, and preferably in a range of 20° to 40°.

The microneedle 13, formed using the frustum-shaped protrusion 15 and the cone-shaped recess 51 having the shape relationships described above, can be expressed as having a wedge-like shape that protrudes from the frustum-shaped protrusion 15, as illustrated in FIG. 14. Alternatively, the frustum-shaped protrusion 15 and the microneedle 13 can be expressed as having a mushroom-like shape. Only the microneedles 13 remain in the inner part of the skin, and the foundation 14 and the frustum-shaped protrusions 15 are removed from the skin after the drug has been administered. On this point, it is clear that the shape of the microneedles 13, specifically the microneedles 13 protruding from the frustum-shaped protrusions 15, makes it more likely for the microneedles 13 to remain in the inner part of the skin.

Note that the length h4 of the protruding portion (the length from the tip surface 15a of the frustum-shaped protrusion 15 to the bottom 13c of the microneedle 13) is preferably not greater than 200 μm. If the length h4 is increased, the protruding portions will remain on the frustum-shaped protrusions 15 when the microneedles 13 are administered and, as a result, dosage error may increase.

(4-6) Modification Example F

In the embodiment described above, a case is described in which the frustum-shaped protrusions 15 fit into the cone-shaped recesses 51 without any gaps. However, as illustrated in FIG. 15, a configuration is possible in which the frustum-shaped protrusions 15 are supported on the cone-shaped recesses 51. To realize this configuration, the angle θ1 of generating line of the side surface 15b of the frustum-shaped protrusion 15 illustrated in FIG. 15 is formed so as to be larger than the angle θ2 of generating line of the side wall 51b of the cone-shaped recess 51, and an intermediate width W5 of the frustum-shaped protrusion 15 is formed so as to be wider than the width W4 of the opening in the surface 50a of the cone-shaped recess 51. In this case, the angle θ1 of generating line of the side surface 15b of the frustum-shaped protrusion 15 (see FIG. 3) is preferably set to an angle obtained by adding an angle selected from a range of, for example, 5° to 15° to the angle θ2 of generating line of the side wall 51b of the cone-shaped recess 51 (see FIG. 4). From the perspectives of ease of production and facilitating penetration into the skin, the angle θ2 is set in a range of 10° to 50°, and preferably in a range of 20° to 40°.

Figure 16:
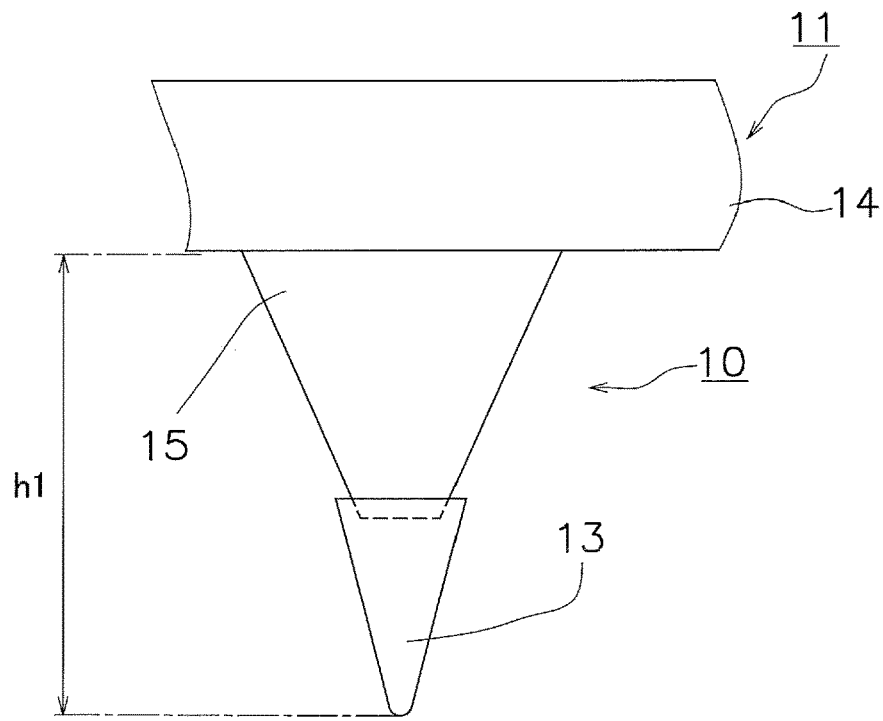
FIG. 16 is a partially enlarged side view schematically illustrating one of the microneedles formed by the mold and the base material illustrated in FIG. 15.

The microneedles 13, formed using the frustum-shaped protrusion 15 and the cone-shaped recess 51 having the shape relationships described above, can be expressed as having a wedge-like shape protruding from the frustum-shaped protrusion 15, as illustrated in FIG. 16. Alternatively, the frustum-shaped protrusion 15 and the microneedle 13 can be expressed as having a mushroom-like shape. Only the microneedles 13 remain in the inner part of the skin, and the foundation 14 and the frustum-shaped protrusions 15 are removed from the skin after the drug has been administered. On this point, it is clear that the shape of the microneedles 13, specifically the microneedles 13 protruding from the frustum-shaped protrusions 15, makes it more likely for the microneedles 13 to remain in the inner part of the skin.

Additionally, as is clear from FIG. 15, the first main surface 14a of the foundation 14 is separated from the surface 50a of the mold 50. By changing the height of the frustum-shaped protrusion 15 and adjusting the gap between the first main surface 14a of the foundation 14 and the surface 50a of the mold 50, it is possible to provide microneedle arrays 10 for which the height h1 of the tip position of the microneedles 13 differs, while still using the same mold 50.

(4-7) Modification Example G

Figure 17:
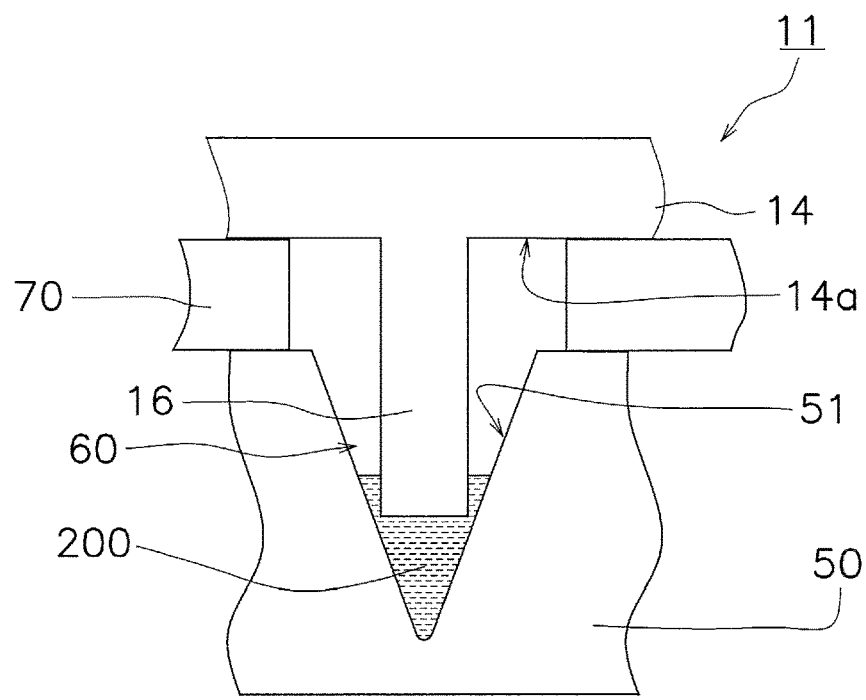
FIG. 17 is a partially enlarged cross-sectional view schematically illustrating a fourth example of the combination of the mold and the base material.
Figure 18:
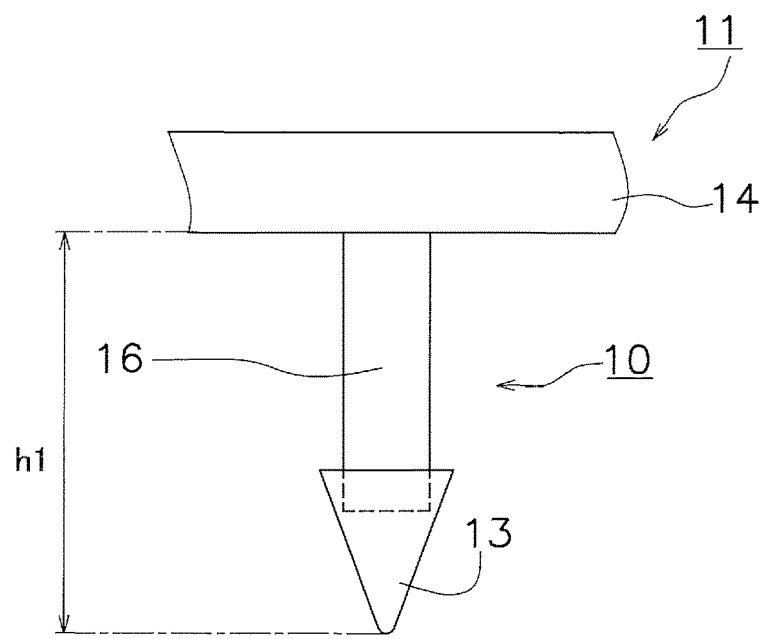
FIG. 18 is a partially enlarged side view schematically illustrating one of the microneedles formed by the mold and the base material illustrated in FIG. 17.

In the embodiment and modification examples A to F described above, a case is described in which the frustum-shaped protrusions 15 and the cone-shaped recesses 51 are used to produce the microneedle array 10. However, as illustrated in FIG. 17, a configuration is possible in which a base material 11 is used in which columnar protrusions 16, instead of the frustum-shaped protrusions 15, are formed on the foundation 14. These columnar protrusions 16 may be round columns or angular columns, or may have a columnar structure for which the cross-sectional shape is a shape other than circular or polygonal. Additionally, the columnar protrusions 16 may include changes in the shape thereof, such as bends or changes in thickness. In a comparison of the microneedle arrays 10 illustrated in FIGS. 16 and 18, it is clear that even though the columnar protrusions 16 and the frustum-shaped protrusions 15 are different, both configurations can provide the wedge-like microneedles 13.

Moreover, the length that the columnar protrusions 16 enter into the cone-shaped recesses 51 may be adjusted using a spacer 70 in order to provide microneedle arrays 10 having different heights h1 of the tip position of the microneedles 13 while using the same mold 50.

(4-8) Modification Example H

Figure 19:
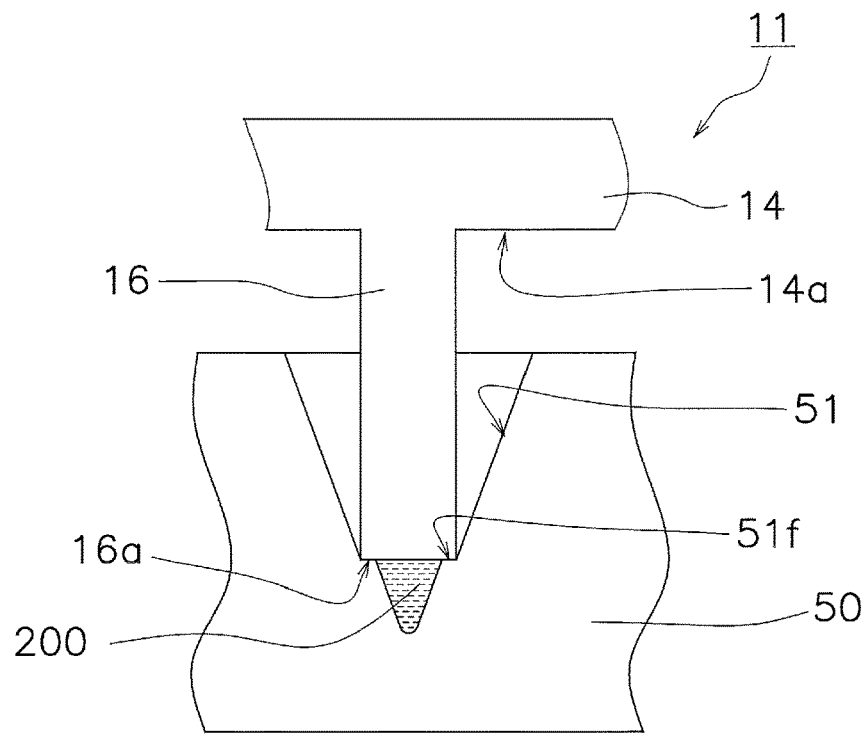
FIG. 19 is a partially enlarged cross-sectional view schematically illustrating a fifth example of the combination of the mold and the base material.

In the embodiment and modification examples A to G described above, a case is described in which a step is formed in the frustum-shaped protrusion 15. However, as illustrated in FIG. 19, a configuration is possible in which a step 51f for mounting the tip surface 16a of the columnar protrusion 16 is formed in the cone-shaped recess 51.

Figure 20:
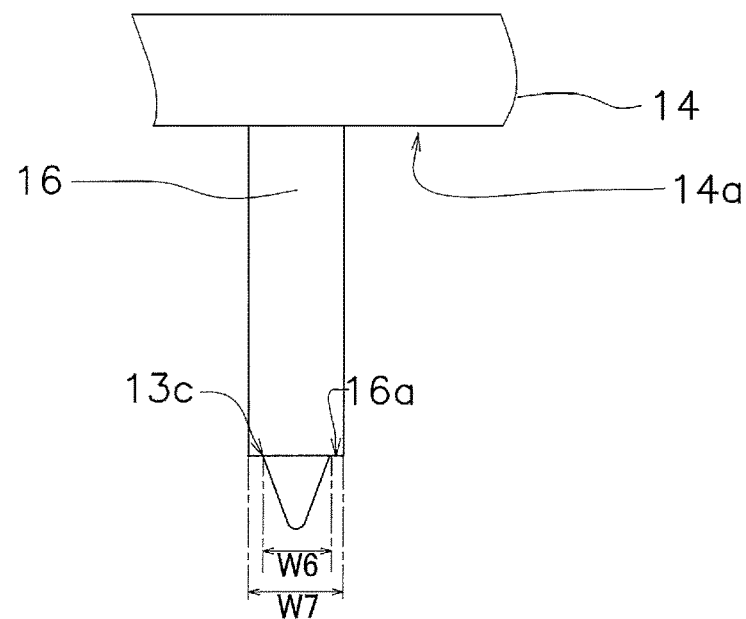
FIG. 20 is a partially enlarged side view schematically illustrating one of the microneedles formed by the mold and the base material illustrated in FIG. 19.

As illustrated in FIG. 20, in the microneedle array 10 according to modification example H, the width W6 of the bottom 13c of the microneedle 13 is smaller than the width W7 of the tip surface 16a of the columnar protrusion 16.

In modification example H, a case is described in which the columnar protrusions 16 are used, but the frustum-shaped protrusions 15 can be used instead of the columnar protrusions 16.

(4-9) Modification Example I

In modification example H, the tip surface 16a of the columnar protrusion 16 is caused to abut against the cone-shaped recess 51 by forming the step 51f in the cone-shaped recess 51. As a result, the base material 11 is supported by the side wall 51b of the cone-shaped recess 51.

Figure 21:
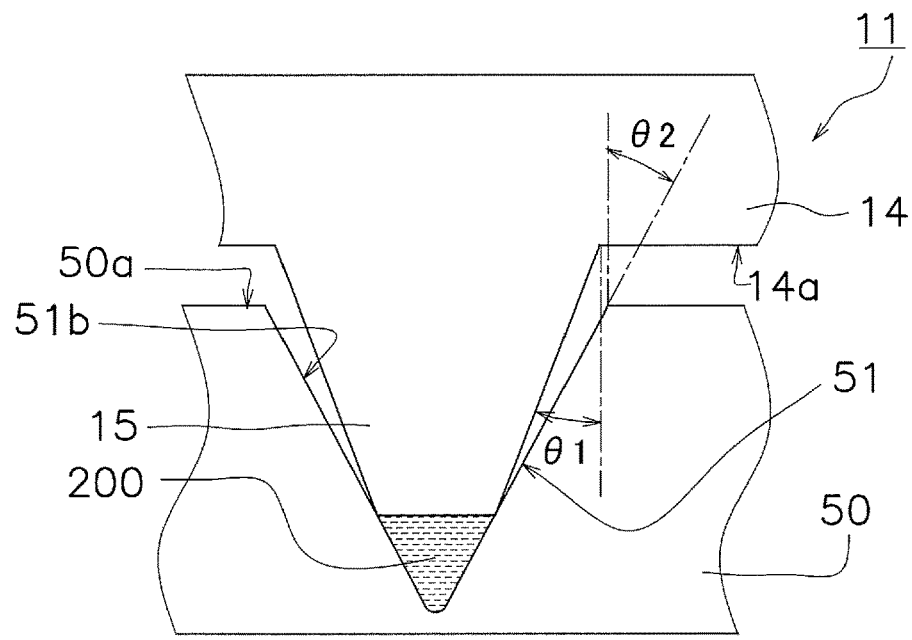
FIG. 21 is a partially enlarged cross-sectional view schematically illustrating a sixth example of the combination of the mold and the base material.

As with modification example H, to support the base material 11 on the side wall 51b of the cone-shaped recess 51, as illustrated in FIG. 21, it is sufficient that the angle θ1 of generating line of the side surface 15b of the frustum-shaped protrusion 15 be formed smaller than the angle θ2 of generating line of the side wall 51b of the of the cone-shaped recess 51. Moreover, the columnar protrusion may be used instead of the frustum-shaped protrusion 15. In this case as well, a variety of microneedle arrays 10 can be formed, while using the same mold 50, by changing the injection amount of the raw material liquid 200 and/or the shapes of the frustum-shaped protrusions 15 and the columnar protrusions 16.

Figure 22:
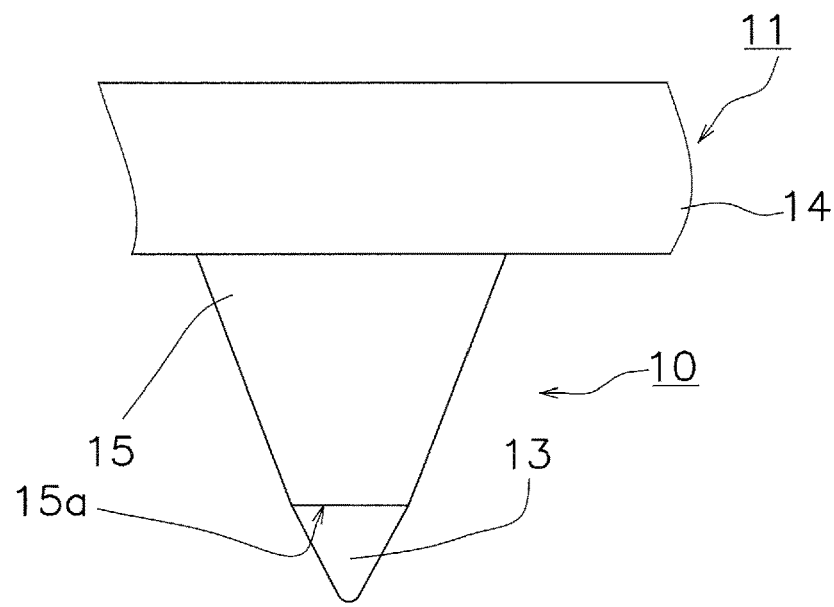
FIG. 22 is a partially enlarged side view schematically illustrating one of the microneedles formed by the mold and the base material illustrated in FIG. 21.

Note that, in this case, the width of the bottom of the microneedle 13 matches the width of the tip surface 15a of the frustum-shaped protrusion 15, as illustrated in FIG. 22.

(4-10) Modification Example J

Figure 23A:
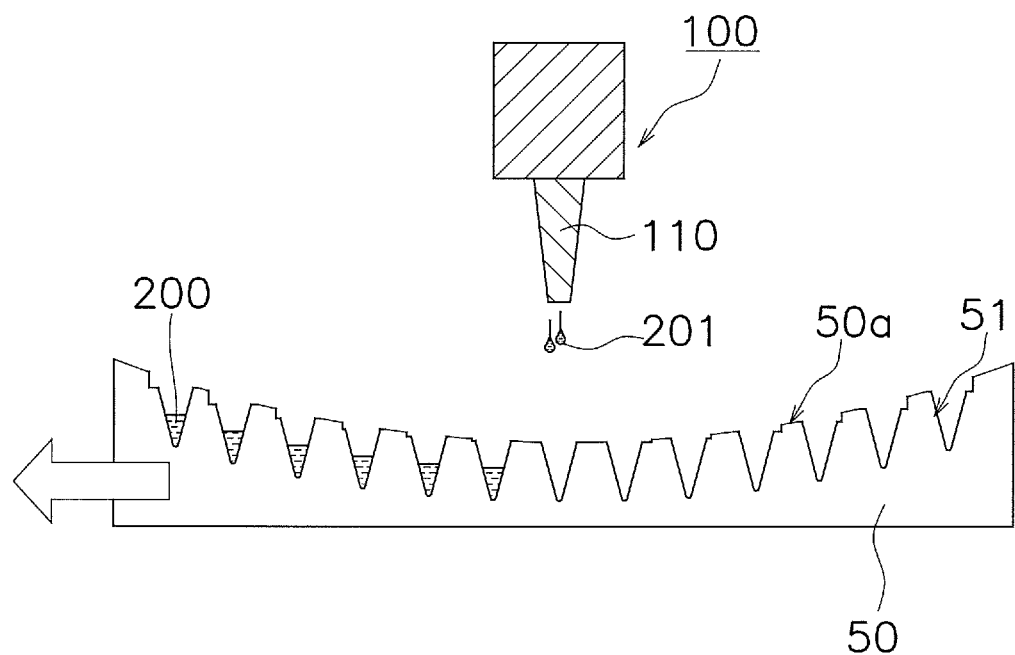
FIG. 23A is a schematic cross-sectional view for describing the production method of a microneedle array for which a first main surface of the base material is curved.
Figure 23B:
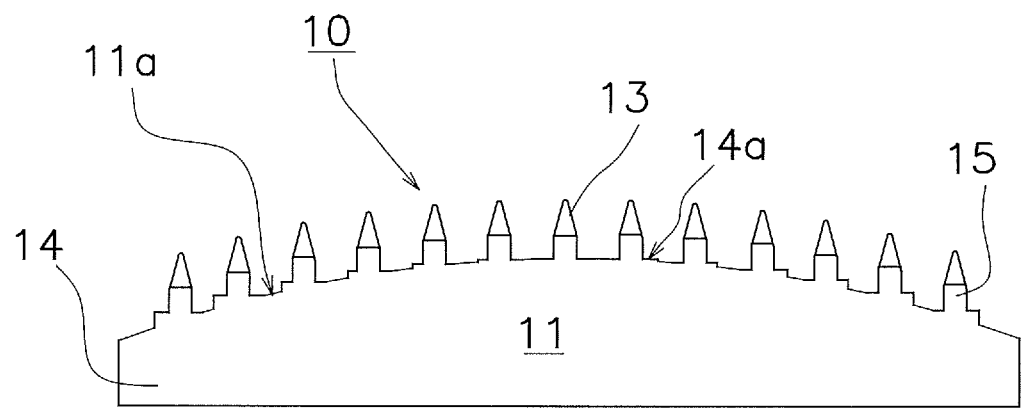
FIG. 23B is a schematic cross-sectional view illustrating an example of a microneedle array produced by the production method illustrated in FIG. 23A.

In the embodiment and modification examples A to I described above, a case is described in which the first main surface 14a of the foundation 14 is flat. However, a configuration is possible in which the first main surface 14a of the foundation 14 (the first main surface 11a of the base material 11) is curved, as illustrated in FIG. 23B. To form the microneedle array 10 illustrated in FIG. 23B, in one example, a mold 50 having a curved surface 50a, such as that illustrated in FIG. 23A, is prepared. Then, as in the embodiment described above, a predetermined number of droplets 201 is injected from the droplet discharge device 110 of the microneedle array production apparatus 100 into each of the cone-shaped recesses 51. Thereafter, the base material 11 having the first main surface 14a that is curved as illustrated in FIG. 23B is overlaid on the mold 50.

When the shape of the curved first main surface 14a corresponds to the shape of the skin to which the microneedle array 10 is to applied, it is more likely that all of the microneedles 13 of the microneedle array 10 will penetrate into the inner part of the skin.

(4-11) Modification Example K

In the embodiment and the modification examples described above, a case is described in which the cone-shaped recess 51 has a cone-shaped or has a step in a portion of the cone-shaped recess 51. However, the shape of the cone-shaped recess is not limited thereto and any shape may be used provided that the shape of the portions other than where the microneedle 13 is formed does not obstruct the overlaying of the base material 11.

(4-12) Modification Example L

Figure 24:
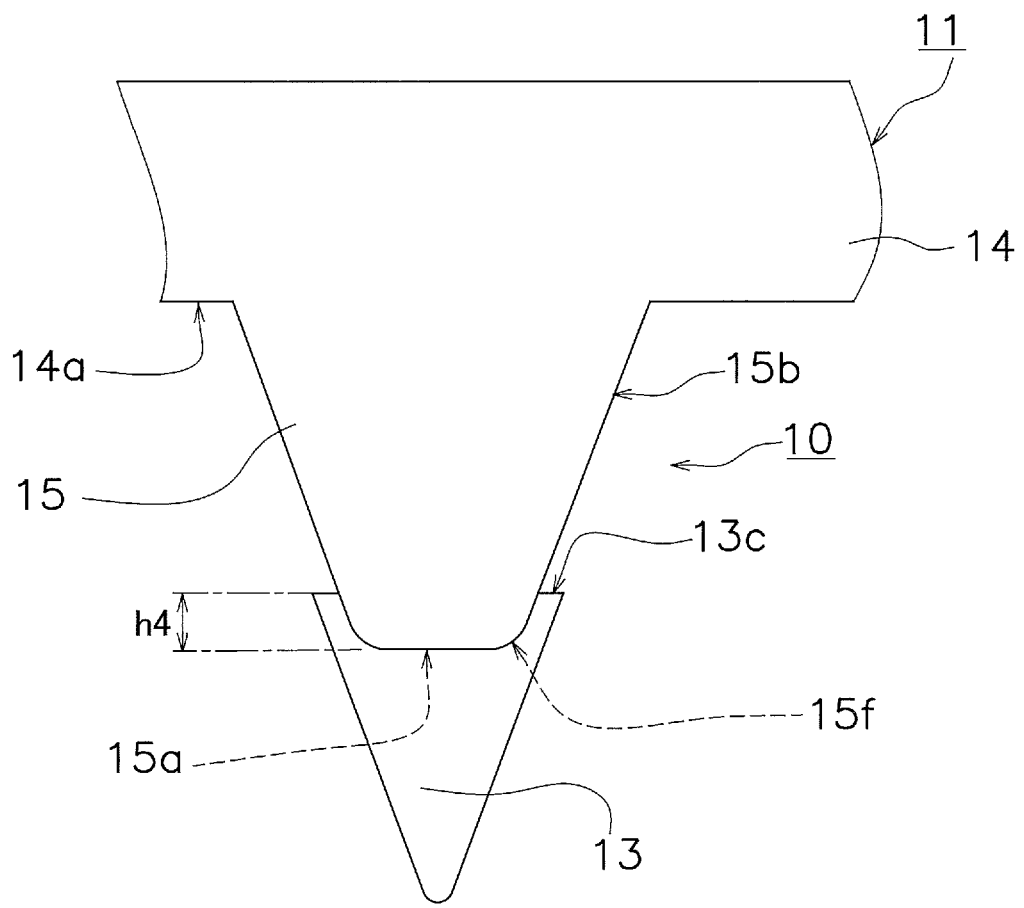
FIG. 24 is a partially enlarged cross-sectional view schematically illustrating a microneedle for a case in which a base material is used that includes a frustum-shaped protrusion, wherein a rounding is formed on the periphery of a tip surface of the frustum-shaped protrusion.

In modification example E, FIG. 14 is used to describe a case in which the microneedles 13 protrude the length h4 from the frustum-shaped protrusions 15. The side surface 15b of the frustum-shaped protrusion 15 illustrated in FIG. 14 is cut away at the tip surface 15a, and the periphery of the tip surface 15a is angular. However, as illustrated in FIG. 24, a configuration is possible in which a rounding 15f is formed such that the boundary portion between the side surface 15b and the tip surface 15a of the frustum-shaped protrusion 15, has a cross-sectional arc shape. The radius of the rounding 15f is preferably set to 50 μm or less. As a result of forming the rounding 15f, the contact area between the microneedle 13 and the frustum-shaped protrusion 15 can be increased, even when the length h4 from the tip surface 15a of the frustum-shaped protrusion 15 to the bottom 13c of the microneedle 13 is the same as in modification example E, for example. As a result, the fixing force between the microneedle 13 and the frustum-shaped protrusion 15 is improved. Moreover, durability of the microneedles 13 against lateral impacts (forces parallel to the first main surface 14a of the foundation 14) is improved. By forming the rounding 15f, the strength of the microneedle array 10 can be improved.

Note that a case is described using FIG. 24 in which the rounding 15f is formed on the periphery of the tip surface 15a of the frustum-shaped protrusion 15. However, in a case in which columnar protrusions are used, the rounding may be formed on the tip surface of the columnar protrusion. In this case as well, the same advantageous effects are obtained as in the case in which the rounding is formed on the frustum-shaped protrusion.

(4-13) Modification Example M

In the embodiment and the modification examples described above, a case is described in which the base material includes a foundation and frustum-shaped protrusions or columnar protrusions. However, the shape of the base material is not limited thereto and a configuration is possible in which the base material further includes a tip foundation on the frustum-shaped protrusion or columnar protrusion.

Figure 25:
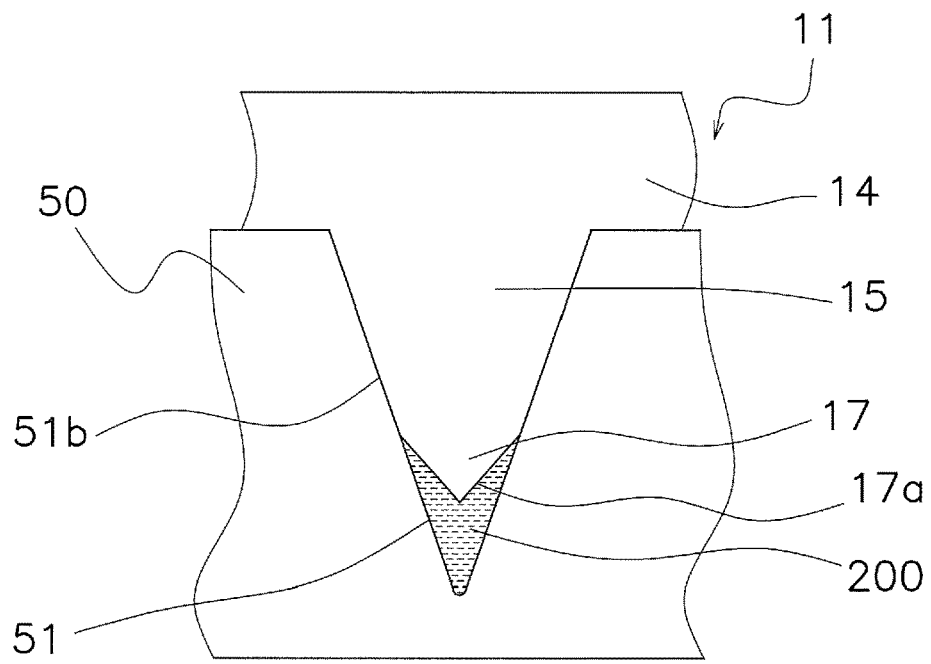
FIG. 25 is a partially enlarged cross-sectional view schematically illustrating a mold and a base material for a case in which a base material is used that includes a frustum-shaped protrusion wherein a tip foundation is formed on the tip surface of the frustum-shaped protrusion.
Figure 26:
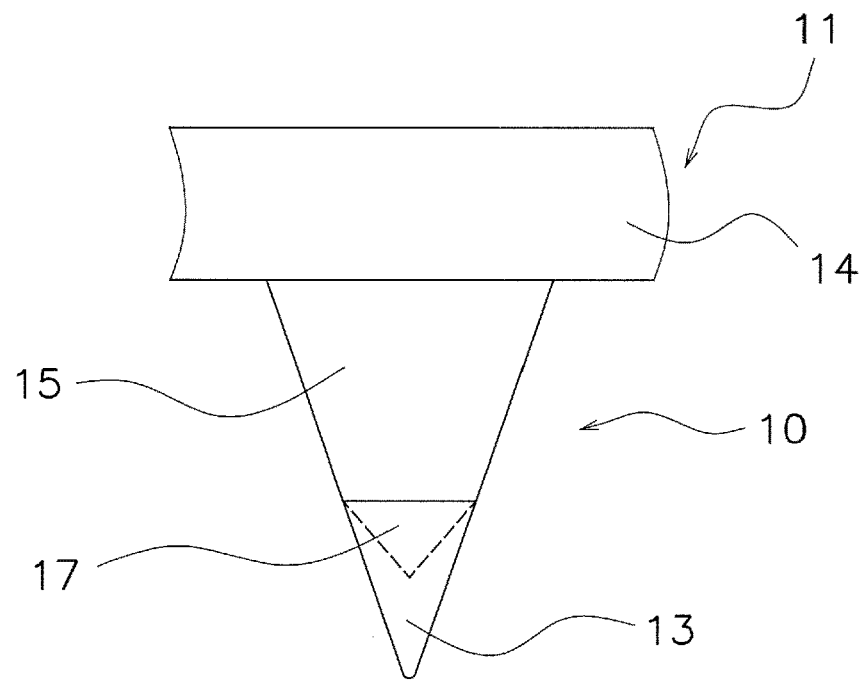
FIG. 26 is a partially enlarged cross-sectional view schematically illustrating one of the microneedles formed by the mold and the base material illustrated in FIG. 25.

Referencing FIG. 25, the base material 11 includes the foundation 14, the frustum-shaped protrusions 15, and tip foundations 17. Each of the tip foundation 17 has a cone-shaped and is formed protruding from the tip surface of the frustum-shaped protrusion 15. The diameter of the bottom surface of the tip foundation 17 is the same as the diameter of the tip surface of the frustum-shaped protrusion 15. An angle of a side surface 17a of the tip foundation 17 is larger than the angle of the side wall 51b of the mold 50, and a tip angle of the tip foundation 17 is larger than the tip angle of the cone-shaped recess 51 of the mold 50. When the base material 11 is overlaid on the mold 50, the frustum-shaped protrusion 15 fits, without gaps, into the side wall 51b of the cone-shaped recess 51, and the tip foundation 17 does not contact the side wall 51b of the cone-shaped recess 51. When the base material 11 is overlaid on the mold 50 after the raw material liquid 200 is discharged into the cone-shaped recess 51 of the mold 50, the tip foundation 17 is submerged in the raw material liquid 200. Referencing FIG. 26, the completed microneedle array 10 includes the microneedles 13 fixed to the surfaces of the tip foundations 17. Since the tip foundations 17 are embedded in the microneedles 13, it is possible to visually distinguish the frustum-shaped protrusions 15 and the microneedles 13 from the outside. In this modification example, providing the tip foundation 17 leads to an increase in the contact area with the raw material liquid 200 and, as a result, the fixing force between the dried microneedles 13 (i.e., the cone-shaped tips) and the frustum-shaped protrusions and the tip foundations 17 improves and the microneedles 13 are less likely to fall off. Additionally, since the tip foundations 17 have a shape that bites into the microneedles 13, the microneedles 13 are less likely to fall off of the tip foundations 17.

In modification example M, the diameter of the tip surface of the frustum-shaped protrusion 15 and the diameter of the bottom surface of the tip foundation 17 are the same, but the size and shape of the tip foundation 17 are not limited thereto. A configuration is possible in which the tip foundation 17 has a cone-shaped in which the diameter of the bottom surface of the tip foundation 17 is smaller than the diameter of the tip surface of the frustum-shaped protrusion 15. Additionally, the tip foundation 17 may have a truncated cone-shaped, a truncated pyramid shape, a cylindrical shape, a prismatic shape, a hemispherical shape, or a combination thereof. Moreover, the columnar protrusions may be used instead of the frustum-shaped protrusions 15.

Furthermore, in modification example M, a case is described in which the frustum-shaped protrusions 15 fit into the cone-shaped recesses 51b without gaps. However, as illustrated in FIGS. 13, 15, 17, and 21, the tip foundation 17 may be provided even when there are gaps between the frustum-shaped protrusions 15 or the columnar shape protrusions 16 and the cone-shaped recesses 51. Additionally, the surface of the tip foundation 17 may be roughened, a dimple may be formed in the surface of the tip foundation 17, and the like. Moreover, the tip foundation 17 can be formed on the tip surface of the frustum-shaped protrusion 15, even when the first main surface 14a of the foundation 14 is curved as illustrated in FIG. 23, and/or when the rounding 15f is formed at the boundary portion between the side surface 15b and the tip surface 15a of the frustum-shaped protrusion 15 as illustrated in FIG. 24.

While only selected embodiments have been chosen to illustrate the present (advancement, it will be apparent to those skilled in the art from this disclosure that various changes and modifications can be made herein without departing from the scope of the disclosure as defined in the appended claims. Furthermore, the foregoing descriptions of the embodiments according to the present disclosure are provided as examples only, and not for the purpose of limiting the disclosure as defined by the appended claims and their equivalents. Thus, the scope of the disclosure is not limited to the disclosed embodiments.

What is claimed is:

1. A method of producing a microneedle array, the method comprising:
   a preparation step of preparing a foundation that is insoluble or sparingly soluble with respect to a raw material liquid, the foundation including a plurality of frustum-shaped protrusions or a plurality of columnar protrusions on a first main surface thereof;
   an injection step of injecting a predetermined amount of the raw material liquid into each cone-shaped recess of a mold having a plurality of cone-shaped recesses, the predetermined amount being less than a volume of the cone-shaped recess, and filling a part of each of the plurality of cone-shaped recesses with the raw material liquid;
   a tip forming step of stacking the foundation prepared in the preparation step before the tip forming step on the mold, mating the plurality of frustum-shaped protrusions or columnar protrusions with the plurality of cone-shaped recesses that are shaped to match the plurality of frustum-shaped protrusions or columnar protrusions of the foundation by the filling in the injection step, drying the raw material liquid in the plurality of cone-shaped recesses after stacking the foundation on the mold thereby fixing a plurality of cone-shaped tips that are dissolvable in an inner part of skin to a tip surface of each of the plurality of frustum-shaped protrusions or columnar protrusions; and
   a mold release step of removing the foundation from the mold, and pulling out a microneedle array in which the cone-shaped tips are fixed to each of the frustum-shaped protrusions or the columnar protrusions of the foundation and the cone-shaped tips are formed at a position a predetermined height away from the first main surface of the foundation.

2. The method of producing a microneedle array according to claim 1, further comprising:
   an inspection step of immersing the microneedle array in a solvent capable of dissolving the cone-shaped tips to dissolve the plurality of cone-shaped tips and make a solution, and analyzing a component contained in each of the microneedle array based on the solution.

3. The method of producing a microneedle array according to claim 2, wherein
   in the preparation step, the plurality of frustum-shaped protrusions or the plurality of columnar protrusions of the foundation are formed by injection molding.

4. The method of producing a microneedle array according to claim 3, wherein
   in the preparation step, a roughening treatment is performed or a dimple is formed at a contacting portion of the plurality of frustum-shaped protrusions or the plurality of columnar protrusions, the contacting portion being where the cone-shaped tips are to be fixed.

5. The method of producing a microneedle array according to claim 3, wherein
   the raw material liquid includes water as a solvent, and
   in the preparation step, a hydrophilic treatment is performed on a contacting portion of the plurality of frustum-shaped protrusions or the plurality of columnar protrusions, the contacting portion being where the cone-shaped tips are to be fixed, such that a hydrophilicity of the contacting portion is made greater than a hydrophilicity of a material of the foundation.

6. The method of producing a microneedle array according to claim 1, wherein
   in the tip forming step, while the foundation is overlaid on the mold, a gap is formed between a side wall of each of the cone-shaped recesses and a side surface of each of the frustum-shaped protrusions or the columnar protrusions and the raw material liquid is fed into the gap, thereby forming the cone-shaped tip up to the side surface of each of the frustum-shaped protrusions or the columnar protrusions above a position that is a predetermined height away from the first main surface.

7. The method of producing a microneedle array according to claim 1, wherein
   in the tip forming step, the foundation and the mold are arranged such that the side surface of each of the frustum-shaped protrusions or the columnar protrusions abuts against a side wall of each of the cone-shaped recesses due to the foundation being overlaid on the mold.

8. The method of producing a microneedle array according to claim 1, wherein
   in the preparation step, the plurality of frustum-shaped protrusions or the plurality of columnar protrusions of the foundation are formed by injection molding.

9. The method of producing a microneedle array according to claim 8, wherein
   in the preparation step, a roughening treatment is performed or a dimple is formed at a contacting portion of the plurality of frustum-shaped protrusions or the plurality of columnar protrusions, the contacting portion being where the cone-shaped tips are to be fixed.

10. The method of producing a microneedle array according to claim 8, wherein the raw material liquid includes water as a solvent, and in the preparation step, a hydrophilic treatment is performed on a contacting portion of the plurality of frustum-shaped protrusions or the plurality of columnar protrusions, the contacting portion being where the cone-shaped tips are to be fixed, such that a hydrophilicity of the contacting portion is made greater than a hydrophilicity of a material of the foundation.

11. The method of producing a microneedle array according to claim 1, wherein the frustum-shaped protrusions or the columnar protrusions have tip foundations protruding from the tip surface of each of the frustum-shaped protrusions or the columnar protrusions so as not to contact a wall surface of each of the frustum-shaped recesses, and in the tip forming step, the cone-shaped tip is fixed to a surface of the tip foundation instead of to the tip surface, or the cone-shaped tip is fixed to a portion of the tip surface and the surface of the tip foundation.

12. The method of producing a microneedle array according to claim 1, wherein in the injection step, the predetermined amount of the raw material liquid is injected into each cone-shaped recess such that the raw material liquid does not overflow from the cone-shaped recess.

13. The method of producing a microneedle array according to claim 1, wherein the foundation is a solid resin foundation made of thermoplastic resin.

14. The method of producing a microneedle array according to claim 1, wherein in the tip forming step, the foundation is stacked such that the tip surface of each of the plurality of frustum-shaped protrusions or columnar protrusions of the foundation faces downward and the tip surface is dipped into the raw material liquid filled in the mold.

15. The method of producing a microneedle array according to claim 3, wherein before the injection molding, the mold is prepared to have a shape that corresponds to the shape of the foundation already prepared in the preparation step.

16. The method of producing a microneedle array according to claim 1, wherein pointed shapes are absent on the tip surface of each of the plurality of frustum-shaped protrusions or columnar protrusions of the foundation injection-molded and facing downward.

* * * * *